(12) United States Patent
Lok et al.

(10) Patent No.: US 6,271,343 B1
(45) Date of Patent: *Aug. 7, 2001

(54) MAMMALIAN CYTOKINE-LIKE RECEPTOR 5

(75) Inventors: Si Lok; Scott R. Presnell, both of Seattle; Anna C. Jelmberg, Issaquah; Teresa Gilbert, Auburn; Theodore E. Whitmore, Redmond; Donald C. Foster, Lake Forest Park; Robyn L. Adams, Bellevue; Joyce M. Lehner, Seattle, all of WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 09/071,224

(22) Filed: May 1, 1998

Related U.S. Application Data

(60) Provisional application No. 60/045,287, filed on May 1, 1997, and provisional application No. 60/074,721, filed on Feb. 13, 1998.

(51) Int. Cl.⁷ .................................................. C07K 14/715
(52) U.S. Cl. .......................... 530/324; 530/326; 530/300; 530/350
(58) Field of Search ..................................... 530/350, 324, 530/326, 351; 514/2, 8, 12; 424/85.1; 930/100

(56) References Cited

U.S. PATENT DOCUMENTS 5,783,672 * 7/1998 Masley et al. ........................ 530/350

FOREIGN PATENT DOCUMENTS

| 98/11225 | 3/1998 | (WO) . |
| 98/31811 | 7/1998 | (WO) . |

OTHER PUBLICATIONS

Bravo et al, Cell 1990, 63, p 1149–57 (sequence alignment).*
Marra et al., WashU–HHMI Mouse EST Project, 1996.
Elson et al., *J. Immunol. 161*: 1371–1379, 1998.

* cited by examiner

*Primary Examiner*—Elizabeth Kemmerer
*Assistant Examiner*—Sandra Wegert
(74) *Attorney, Agent, or Firm*—Paul G. Lunn, Esq.

(57) ABSTRACT

Novel receptor polypeptides, polynucleotides encoding the polypeptides, and related compositions. The polypeptides of the present invention can be used to down-regulate their natural ligands. The polynucleotides and subsequences thereof can be used as diagnostic probes to determine if chromosome 19 is mutated. The antibodies which bind to the polypeptides can be used to purify the receptors and to inhibit the binding of the ligands onto the receptors.

2 Claims, No Drawings

US 6,271,343 B1

MAMMALIAN CYTOKINE-LIKE RECEPTOR 5

This application claims benefit of provisional applications No. 60/045,287, filed May 1, 1997 and No. 60,074,721, filed Feb. 13, 1998.

BACKGROUND OF THE INVENTION

Proliferation and differentiation of cells of multicellular organisms are controlled by hormones and polypeptide growth factors. These diffusable molecules allow cells to communicate with each other and act in concert to form cells and organs, and to repair and regenerate damaged tissue. Examples of hormones and growth factors include the steroid hormones (e.g. estrogen, testosterone), parathyroid hormone, follicle stimulating hormone, the interleukins, platelet derived growth factor (PDGF), epidermal growth factor (EGF), granulocyte-macrophage colony stimulating factor (GM-CSF), erythropoietin (EPO) and calcitonin.

Hormones and growth factors influence cellular metabolism by binding to receptors. Receptors may be integral membrane proteins that are linked to signaling pathways within the cell, such as second messenger systems. Other classes of receptors are soluble molecules, such as the transcription factors.

Of particular interest are receptors for cytokines, molecules that promote the proliferation and/or differentiation of cells. Examples of cytokines include erythropoietin (EPO), which stimulates the development of red blood cells; thrombopoietin (TPO), which stimulates development of cells of the megakaryocyte lineage; and granulocyte-colony stimulating factor (G-CSF), which stimulates development of neutrophils. These cytokines are useful in restoring normal blood cell levels in patients suffering from anemia or receiving chemotherapy for cancer. The demonstrated in vivo activities of these cytokines illustrates the enormous clinical potential of, and need for, other cytokines, cytokine agonists, and cytokine antagonists.

SUMMARY OF THE INVENTION

The present invention addresses this need by providing a novel mammalian cytokine-like receptor called mammalian Zcytor5, and related compositions and methods. Within one aspect, the present invention provides an isolated human polynucleotide encoding a ligand-binding human receptor polypeptide. The polypeptide comprises a sequence of amino acids containing (a) the amino acid residues of SEQ ID NO: 17, residues 35 to 422 of SEQ ID NO:2; (b) allelic variants of (a); and (c) sequences that are at least 90%, 95% or 99% identical to (a) or (b). In an alternative embodiment, the polypeptide is comprised of amino acid residues 30 to and including amino acid residue 422 of SEQ ID NO:2.

The present invention also provides for a polynucleotide encoding another allelic variant of SEQ ID NO: 2 which is a human polypeptide receptor and is defined by SEQ ID NO: 4 in particular the polypeptide comprised of a sequence of amino acids containing (a) the amino acid residues of SEQ ID NO: 18, residues 34 to 425 of SEQ ID NO:4; (b) allelic variants of (a); and (c) sequences that are at least 90%, 95% or 99% identical to (a) or (b). In an alternative embodiment, the polypeptide is comprised of amino acid residues 29 to and including amino acid residue 425 of SEQ ID NO:4.

Other polynucleotides of the present invention encode the amino acid sequence of SEQ ID NO:21 which is a soluble receptor of SEQ ID NO:17 that does not contain a C-terminus phosphatidylinositol signal sequence; the amino acid sequence of SEQ ID NO: 20 is a Zcytor5 polypeptide of SEQ ID NO:2 having an alternative N-terminus cleavage site; SEQ ID NO: 22 which has an alternative N-terminus cleavage site of the Zcytor5 polypeptide of SEQ ID NO:4; SEQ ID NO:23 which is an amino acid of SEQ ID NO:18 that does not contain a C-terminus phosphatidylinositol signal sequence and the amino acid sequences defined by SEQ ID NOs: 24–31 which are variants of the Zcytor5 polypeptide of SEQ ID NO:4.

Another embodiment of the present invention is a polynucleotide which encodes rat Zcytor5. In particular, a polynucleotide is claimed which encodes a rat polypeptide containing (a) the amino acid sequence of SEQ ID NO: 19 residues 41 to 425 of SEQ ID NO:6; (b) allelic variants of (a); and (c) sequences that are at least 90%, 95% or 99% identical to (a) or (b).

Within a second aspect of the invention there is provided an expression vector comprising (a) a transcription promoter; (b) a DNA segment encoding a secretory peptide and a ligand-binding Zcyotor5 receptor polypeptide, containing an amino acid sequence as described above.

Within a third aspect of the invention there is provided a cultured eukaryotic cell into which has been introduced an expression vector as disclosed above, wherein said cell expresses a mammalian Zcytor5 receptor polypeptide encoded by the DNA segment.

Within a fourth aspect of the invention there is provided an isolated polypeptide. The polypeptide comprises a sequence of amino acids containing (a) the amino acid sequence of SEQ ID NO: 17, residues 35 to 422 of SEQ ID NO:2; (b) allelic variants of (a); and (c) sequences that are at least 90%, 95% or 99% identical to (a) or (b). In an alternative embodiment, the polypeptide is comprised of amino acid residues 30 to and including amino acid residue 422 of SEQ ID NO:2.

The present invention also provides for another allelic variant of SEQ ID NO: 2 which is a human polypeptide receptor and is defined by SEQ ID NO: 4 in particular the polypeptide is comprised of a sequence of amino acids containing (a) the amino acid sequence of SEQ ID NO: 18, residues 34 to 425 of SEQ ID NO:4; (b) allelic variants of (a); and (c) sequences that are at least 90%, 95% or 99% identical to (a) or (b). In an alternative embodiment, the polypeptide is comprised of residues 29 to 425 of SEQ ID NO: 4.

Another embodiment of the present invention is a rat Zcytor5 polypeptide containing (a) the amino acid sequence of SEQ ID NO: 19, residues 41 to 425 of SEQ ID NO:6; (b) allelic variants of (a); and (c) sequences that are at least 80% identical to (a) or (b).

Within a further aspect of the invention there is provided a chimeric polypeptide consisting essentially of a first portion and a second portion joined by a peptide bond. The first portion of the chimeric polypeptide consists essentially of a Zcytor5 receptor polypeptide as described above. The invention also provides expression vectors encoding the chimeric polypeptides and host cells transfected to produce the chimeric polypeptides.

The invention also provides a method for detecting a ligand within a test sample, comprising contacting a test sample with a Zcytor5 polypeptide as disclosed above, and detecting binding of the polypeptide to ligand in the sample. The polypeptide can be membrane bound within a cultured cell, wherein the detecting step comprises measuring a biological response in the cultured cell. Within another embodiment, the polypeptide is immobilized on a solid support.

Within an additional aspect of the invention there is provided an antibody that specifically binds to a polypeptide as disclosed above and an anti-idiotypic antibody of an antibody which specifically binds to a Zcytor5 antibody, also a method for producing an antibody to Zcytor5.

An additional embodiment of the present invention relates to a peptide or polypeptide which has the amino acid sequence of an epitope-bearing portion of a Zcytor5 polypeptide having an amino acid sequence described above. Peptides or polypeptides having the amino acid sequence of an epitope-bearing portion of a Zcytor5 polypeptide of the present invention include portions of such polypeptides with at least nine, preferably at least 15 and more preferably at least 30 to 50 amino acids, although epitope-bearing polypeptides of any length up to and including the entire amino acid sequence of a polypeptide of the present invention described above are also included in the present invention. Examples of said polypeptides are defined by the amino acid sequences of SEQ ID NOs: 32–37.

DETAILED DESCRIPTION OF THE INVENTION

The teachings of all of the references cited in the present specification are incorporated in their entirety herein by reference.

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A [Nilsson et al, *EMBO J.* 4:1075 (1985); Nilsson et al., *Methods Enzymol.* 198:3 (1991)], glutathione S transferase [Smith and Johnson, *Gene* 67:31 (1988)], Glu-Glu affinity tag [Grussenmeyer et al., *Proc. Natl. Acad. Sci. USA* 82:7952–4 (1985)], substance P, FLAG™ peptide (Hopp et al., *Biotechnology* 6:1204–10 (1988), streptavidin binding peptide, or other antigenic epitope or binding domain. See, in general, Ford et al., *Protein Expression and Purification* 2: 95–107 (1991). DNAs encoding affinity tags are available from commercial suppliers (e.g., Pharmacia Biotech, Piscataway, N.J.).

The term "allelic variant" denotes any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of $<10^9$ $M^{-1}$.

The term "complements of a polynucleotide molecule" is a polynucleotide molecule having a complementary base sequence and reverse orientation as compared to a reference sequence. For example, the sequence 5' ATGCACGGG 3' is complementary to 5' CCCGTGCAT 3'.

The term "contig" denotes a polynucleotide that has a contiguous stretch of identical or complementary sequence to another polynucleotide. Contiguous sequences are said to "overlap" a given stretch of polynucleotide sequence either in their entirety or alone a partial stretch of the polynucleotide.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art, for example, Dynan and Tijan, *Nature* 316:774–78 (1985).

An "isolated" polypeptide or protein is a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. When used in this context, the term "isolated" does not exclude the presence of the same polypeptide in alternative physical forms, such as dimers or alternatively glycosylated or derivatized forms.

"Operably linked", when referring to DNA segments, indicates that the segments are arranged so that they function in concert for their intended purposes, e.g. transcription initiates in the promoter and proceeds through the coding segment to the terminator.

The term "ortholog" (or "species homolog") denotes a polypeptide or protein obtained from one species that has homology to an analogous polypeptide or protein from a different species.

The term "paralog" denotes a polypeptide or protein obtained from a given species that has homology to a distinct polypeptide or protein from that same species.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules.

A "polypeptide" is a polymer of amino acid residues joined by peptide bonds, whether produced naturally or synthetically. Polypeptides of less than about 10 amino acid residues are commonly referred to as "peptides".

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The term "receptor" denotes a cell-associated protein that binds to a bioactive molecule (i.e., a ligand) and mediates the effect of the ligand on the cell. Membrane-bound receptors are characterized by a multi-domain structure comprising an extracellular ligand-binding domain and an intracellular effector domain that is typically involved in signal transduction. Binding of ligand to receptor results in a conformational change in the receptor that causes an interaction between the effector domain and other molecule(s) in the cell. This interaction in turn leads to an alteration in the metabolism of the cell. Metabolic events that are linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids. In general, receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor).

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a protein encoded by a splice variant of an mRNA transcribed from a gene.

A "soluble receptor" is a receptor polypeptide that is not bound to a cell membrane. Soluble receptors are most commonly ligand-binding receptor polypeptides that lack transmembrane and cytoplasmic domains. Soluble receptors can comprise additional amino acid residues, such as affinity tags that provide for purification of the polypeptide or provide sites for attachment of the polypeptide to a substrate, or immunoglobulin constant region sequences. Many cell-surface receptors have naturally occurring, soluble counterparts that are produced by proteolysis or translated from alternatively spliced mRNAs. Receptor polypeptides are said to be substantially free of transmembrane and intracellular polypeptide segments when they lack sufficient portions of these segments to provide membrane anchoring or signal transduction, respectively.

The present invention is based in part upon the discovery of a novel DNA sequence that encodes a protein having the structure of a cytokine receptor, including the conserved WSXWS motif. Analysis of the tissue distribution of the mRNA corresponding to this novel DNA showed that expression was present in highest amounts in placenta, thyroid, heart and skeletal muscle with lower levels in prostate and trachea.

Cytokine receptors subunits are characterized by a multi-domain structure comprising a ligand-binding domain and an effector domain that is typically involved in signal transduction. Multimeric cytokine receptors include homodimers (e.g., PDGF receptor $\alpha\alpha$ and $\beta\beta$ isoforms, erythropoietin receptor, MPL [thrombopoietin receptor], and G-CSF receptor), heterodimers whose subunits each have ligand-binding and effector domains (e.g., PDGF receptor $\alpha\beta$ isoform), and multimers having component subunits with disparate functions (e.g., IL-2, IL-3, IL-4, IL-5, IL-6, IL-7, and GM-CSF receptors). Some receptor subunits are common to a plurality of receptors. For example, the AIC2B subunit, which cannot bind ligand on its own but includes an intracellular signal transduction domain, is a component of IL-3 and GM-CSF receptors. Many cytokine receptors can be placed into one of four related families on the basis of their structures and functions. Hematopoietic receptors, for example, are characterized by the presence of a domain containing conserved cysteine residues and the WSXWS motif. Additional domains, including protein kinase domains; fibronectin type III domains; and immunoglobulin domains, which are characterized by disulfide-bonded loops, are present in certain hematopoietic receptors. Cytokine receptor structure has been reviewed by Urdal, *Ann. Reports Med. Chem.* 26:221–228 (1991) and Cosman, *Cytokine* 5:95–106 (1993). It is generally believed that under selective pressure for organisms to acquire new biological functions, new receptor family members arose from duplication of existing receptor genes leading to the existence of multi-gene families. Family members thus contain vestiges of the ancestral gene, and these characteristic features can be exploited in the isolation and identification of additional family members. The cytokine receptor superfamily is subdivided as shown in Table 1.

TABLE 1

Cytokine Receptor Superfamily

Immunoglobulin family

CSF-1 receptor
MGF receptor
IL-1 receptor
PDGF receptor
Hematopoietin family erythropoietin receptor
G-CSF receptor
IL-2 receptor b-subunit
IL-3 receptor
IL-4 receptor
IL-5 receptor
IL-6 receptor
IL-7 receptor
IL-9 receptor
GM-CSF receptor a-subunit
GM-CSF receptor b-subunit
Prolactin receptor
CNTF receptor Oncostatin M receptor
Leukemia inhibitory factor receptor
Growth hormone receptor
MPL
Leptin receptor
TNF receptor family TNF (p80) receptor
TNF (p60) receptor
TNFR-RP
CD27
CD30
CD40
4-1BB
OX-40
Fas
NGF receptor
Other IL-2 receptor α-subunit
IL-15 receptor α-subunit
IFN-γ receptor Cell-surface cytokine receptors are further characterized by the presence of additional domains. These receptors are anchored in the cell membrane by a transmembrane domain characterized by a sequence of hydrophobic amino acid residues (typically about 21–25 residues), which is commonly flanked by positively charged residues (Lys or Arg). On the opposite end of the protein from the extracellular domain and separated from it by the transmembrane domain is an intracellular domain.

The novel receptor of the present invention was initially identified by the presence of the conserved WSXWS motif. Analysis of a human cDNA clone encoding human Zcytor5 (SEQ ID NO:1) revealed an open reading frame encoding 422 amino acids (SEQ ID NO:2) or an allelic variant reveals an open reading of 425 amino acid residues, SEQ ID NO: 3 and SEQ ID NO:4.

Within preferred embodiments of the invention the isolated polynucleotides will hybridize to similar sized regions of SEQ ID NO:1, SEQ ID NO:3, or SEQ ID NO:5, or a sequence complementary thereto, under stringent conditions. In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Typical stringent conditions are those in which the salt concentration is at least about 0.02 M at pH 7 and the temperature is at least about 60° C. As previously noted, the isolated polynucleotides of the present invention include DNA and RNA. Methods for isolating DNA and RNA are well known in the art. It is generally preferred to isolate RNA from testis, including whole testis tissue extracts or testicular cells, such as Sertoli cells, Leydig cells, spermatogonia, or epididymis, although DNA can also be prepared using RNA from other tissues or isolated as genomic DNA. Total RNA can be prepared using guanidine HCl extraction followed by isolation by centrifugation in a CsCl gradient [Chirgwin et al., *Biochemistry* 18:52–94 (1979)]. Poly (A)+ RNA is prepared from total RNA using the method of Aviv and Leder, *Proc. Natl. Acad. Sci. USA* 69:1408–1412 (1972). Complementary DNA (cDNA) is prepared from poly(A)+ RNA using known methods. Polynucleotides encoding Zcytor5 polypeptides are then identified and isolated by, for example, hybridization or PCR.

Those skilled in the art will recognize that the sequences disclosed in SEQ ID NOS:1, 2, 3,4 represent single alleles of the human and SEQ ID NOs 5 and 6 of the rat Zcytor5 receptors. Allelic variants of these sequences can be cloned by probing cDNA or genomic libraries from different individuals according to standard procedures.

The present invention further provides counterpart receptors and polynucleotides from other species ("species orthologs"). Of particular interest are Zcytor5 receptors from other mammalian species, including murine, porcine, ovine, bovine, canine, feline, equine, and other primate receptors. Species orthologs of the human and macaque Zcytor5 receptors can be cloned using information and compositions provided by the present invention in combination with conventional cloning techniques. For example, a cDNA can be cloned using mRNA obtained from a tissue or cell type that expresses the receptor. Suitable sources of mRNA can be identified by probing Northern blots with probes designed from the sequences disclosed herein. A library is then prepared from mRNA of a positive tissue or cell line. A receptor-encoding cDNA can then be isolated by a variety of methods, such as by probing with a complete or partial human or macaque cDNA or with one or more sets of degenerate probes based on the disclosed sequences. A cDNA can also be cloned using the polymerase chain reaction, or PCR (Mullis, U.S. Pat. No. 4,683,202), using primers designed from the sequences disclosed herein. Within an additional method, the cDNA library can be used to transform or transfect host cells, and expression of the cDNA of interest can be detected with an antibody to the receptor. Similar techniques can also be applied to the isolation of genomic clones.

The polynucleotides of the present invention can be synthesized using DNA synthesizers. Currently the method of choice is the phosphoramidite method. If chemically synthesized double stranded DNA is required for an application such as the synthesis of a gene or a gene fragment, then each complementary strand is made separately. The production of short genes (60 to 80 bp) can be accomplished by synthesizing the complementary strands and then annealing them. For the production of longer genes (>300 bp), however, special strategies must be invoked, because the coupling efficiency of each cycle during chemical DNA synthesis is seldom 100%. To overcome this problem, synthetic genes (double-stranded) are assembled in modular form from single-stranded fragments that are from 20 to 100 nucleotides in length.

One method for building a synthetic gene requires the initial production of a set of overlapping, complementary oligonucleotides, each of which is between 20 to 60 nucleotides long. The sequences of the strands are planned so that, after annealing, the two end segments of the gene are aligned to give blunt or staggered ends. Each internal section of the gene has complementary 3' and 5' terminal extensions that are designed to base pair precisely with an adjacent section. Thus, after the gene is assembled, the only remaining requirement to complete the process is sealing the nicks along the backbones of the two strands with T4 DNA ligase. In addition to the protein coding sequence, synthetic genes can be designed with terminal sequences that facilitate insertion into a restriction endonuclease sites of a cloning vector and other sequences should also be added that contain signals for the proper initiation and termination of transcription and translation. See Glick, Bernard R. and Jack J. Pasternak, *Molecular Biotechnology, Principles & Applications of Recombinant DNA,* (ASM Press, Washington, D.C. 1994), Itakura, K. et al. Synthesis and use of synthetic oligonucleotides. *Annu. Rev. Biochem.* 53 : 323–356 (1984), and Climie, S. et al. *Chemical synthesis of the thymidylate synthase gene. Proc. Natl. Acad. Sci. USA* 87 :633–637 (1990).

Another embodiment of the present invention provides for a peptide or polypeptide comprising an epitope-bearing portion of a polypeptide of the invention. The epitope of the this polypeptide portion is an immunogenic or antigenic epitope of a polypeptide of the invention. A region of a protein to which an antibody can bind is defined as an "antigenic epitope". See for instance, Geysen, H. M. et al., *Proc. Natl. Acad Sci. USA* 81:3998–4002 (1984).

As to the selection of peptides or polypeptides bearing an antigenic epitope (i.e., that contain a region of a protein molecule to which an antibody can bind), it is well known in the art that relatively short synthetic peptides that mimic part of a protein sequence are routinely capable of eliciting an antiserum that reacts with the partially mimicked protein. See Sutcliffe, J. G. et al. *Science* 219:660–666 (1983). Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Peptides that are extremely hydrophobic and those of six or fewer residues generally are ineffective at inducing antibodies that bind to the mimicked protein; longer soluble peptides, especially those containing proline residues, usually are effective.

Antigenic epitope-bearing peptides and polypeptides of the invention are therefore useful to raise antibodies, including monoclonal antibodies, that bind specifically to a polypeptide of the invention. Antigenic epitope-bearing peptides and polypeptides of the present invention contain a sequence of at least nine, preferably between 15 to about 30 amino acids contained within the amino acid sequence of a polypeptide of the invention. However, peptides or polypeptides comprising a larger portion of an amino acid sequence of the invention, containing from 30 to 50 amino acids, or any length up to and including the entire amino acid sequence of a polypeptide of the invention, also are useful for inducing antibodies that react with the protein. Preferably, the amino acid sequence of the epitope-bearing peptide is selected to provide substantial solubility in aqueous solvents (i.e., the sequence includes relatively hydrophilic residues and hydrophobic residues are preferably avoided); and sequences containing proline residues are particularly preferred. All of the polypeptides shown in the sequence listing contain antigenic epitopes to be used according to the present invention, however, specifically designed antigenic epitopes include the peptides defined by SEQ ID NOs:32–37.

The present invention also provides isolated receptor polypeptides that are substantially identical to the receptor polypeptides of SEQ ID NOs: 2, 4 and 6 and their species orthologs. By "isolated" is meant a protein or polypeptide that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. The term "substantially homologous" is used herein to denote polypeptides having 50%, preferably 60%, more preferably at least 80%, sequence identity to the sequences shown in SEQ ID NO:2, 4, or 7 or their species orthologs. Such polypeptides will more preferably be at least 90% identical, and most preferably 95% or more identical to SEQ ID NO:2, 4 or 6 or their species orthologs. Percent sequence identity is determined by conventional methods. See, for example, Altschul et al., *Bull. Math. Bio.* 48: 603–616 (1986) and Henikoff and Henikoff, *Proc. Natl. Acad. Sci. USA* 89:10915–10919 (1992). Briefly, two amino acid sequences are aligned to optimize the alignment scores using a gap opening penalty of 10, a gap extension penalty of 1, and the "blossom 62" scoring matrix of Henikoff and Henikoff (ibid.) as shown in Table 2 (amino acids are indicated by the standard one-letter codes). The percent identity is then calculated as:

$$\frac{\text{Total number of identical matches}}{[\text{length of the longer sequence plus the number of gaps introduced into the longer sequence in order to align the two sequences}]} \times 100$$

TABLE 2

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |

TABLE 2-continued

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

Sequence identity of polynucleotide molecules is determined by similar methods using a ratio as disclosed above.

Polynucleotides, generally a cDNA sequence, of the present invention encode the above-described polypeptides. A cDNA sequence which encodes a polypeptide of the present invention is comprised of a series of codons, each amino acid residue of the polypeptide being encoded by a codon and each codon being comprised of three nucleotides. The amino acid residues are encoded by their respective codons as follows.

Alanine (Ala) is encoded by GCA, GCC, GCG or GCT;

Cysteine (Cys) is encoded by TGC or TGT;

Aspartic acid (Asp) is encoded by GAC or GAT;

Glutamic acid (Glu) is encoded by GAA or GAG;

Phenylalanine (Phe) is encoded by TTC or TTT;

Glycine (Gly) is encoded by GGA, GGC, GGG or GGT;

Histidine (His) is encoded by CAC or CAT;

Isoleucine (Ile) is encoded by ATA, ATC or ATT;

Lysine (Lys) is encoded by AAA, or AAG;

Leucine (Leu) is encoded by TTA, TTG, CTA, CTC, CTG or CTT;

Methionine (Met) is encoded by ATG;

Asparagine (Asn) is encoded by AAC or AAT;

Proline (Pro) is encoded by CCA, CCC, CCG or CCT;

Glutamine (Gln) is encoded by CAA or CAG;

Arginine (Arg) is encoded by AGA, AGG, CGA, CGC, CGG or CGT;

Serine (Ser) is encoded by AGC, AGT, TCA, TCC, TCG or TCT;

Threonine (Thr) is encoded by ACA, ACC, ACG or ACT;

Valine (Val) is encoded by GTA, GTC, GTG or GTT;

Tryptophan (Trp) is encoded by TGG; and

Tyrosine (Tyr) is encoded by TAC or TAT.

It is to be recognized that according to the present invention, when a cDNA is claimed as described above, it is understood that what is claimed are both the sense strand, the anti-sense strand, and the DNA as double-stranded having both the sense and anti-sense strand annealed together by their respective hydrogen bonds. Also claimed is the messenger RNA (mRNA) which encodes the polypeptides of the present invention, and which mRNA is encoded by the above-described cDNA. A messenger RNA (mRNA) will encode a polypeptide using the same codons as those defined above, with the exception that each thymine nucleotide (T) is replaced by a uracil nucleotide (U).

Substantially identical proteins and polypeptides are characterized as having one or more amino acid substitutions, deletions or additions. These changes are preferably of a minor nature, that is conservative amino acid substitutions (see Table 3) and other substitutions that do not significantly affect the folding or activity of the protein or polypeptide; small deletions, typically of one to about 30 amino acids; and small amino- or carboxyl-terminal extensions, such as an amino-terminal methionine residue, a small linker peptide of up to about 20–25 residues, or a small extension that facilitates purification (an affinity tag), such as a polyhistidine tract, protein A, Nilsson et al., *EMBO J.* 4:1075 (1985); Nilsson et al., *Methods Enzymol.* 198:3 (1991), glutathione S transferase, Smith and Johnson, *Gene* 67:31 (1988), or other antigenic epitope or binding domain. See, in general Ford et al., *Protein Expression and Purification* 2: 95–107 (1991. DNAs encoding affinity tags are available from commercial suppliers (e.g., Pharmacia Biotech, Piscataway, N.J.).

TABLE 3

Conservative amino acid substitutions

| | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

Essential amino acids in the receptor polypeptides of the present invention can be identified according to procedures known in the art, such as site-directed mutagenesis or alanine-scanning mutagenesis, Cunningham and Wells, *Science* 244: 1081–1085 (1989); Bass et al., *Proc. Natl. Acad. Sci. USA* 88:4498–4502 (1991). In the latter technique, single alanine mutations are introduced at every residue in the molecule, and the resultant mutant molecules are tested for biological activity (e.g., ligand binding and signal transduction) to identify amino acid residues that are critical to the activity of the molecule. Sites of ligand-receptor interaction can also be determined by analysis of crystal structure as determined by such techniques as nuclear magnetic resonance, crystallography or photoaffinity labeling. See, for example, de Vos et al., *Science* 255:306–312 (1992); Smith et al., *J. Mol. Biol.* 224:899–904 (1992); Wlodaver et al., *FEBS Lett.* 309:59–64 (1992). The identities of essential amino acids can also be inferred from analysis of homologies with related receptors.

Multiple amino acid substitutions can be made and tested using known methods of mutagenesis and screening, such as those disclosed by Reidhaar-Olson and Sauer, *Science* 241:53–57 (1988) or Bowie and Sauer, *Proc. Natl. Acad. Sci. USA* 86:2152–2156 (1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display, e.g., Lowman et al., *Biochem.* 30:10832–10837 (1991); Ladner et al., U.S. Pat. No. 5,223,409; Huse, WIPO Publication WO 92/06204) and region-directed mutagenesis, Derbyshire et al., *Gene* 46:145 (1986); Ner et al., *DNA* 7:127, (1988).

Mutagenesis methods as disclosed above can be combined with high-throughput screening methods to detect activity of cloned, mutagenized receptors in host cells. Preferred assays in this regard include cell proliferation assays and biosensor-based ligand-binding assays, which are described below. Mutagenized DNA molecules that encode active receptors or portions thereof (e.g., ligand-binding fragments) can be recovered from the host cells and rapidly sequenced using modern equipment. These methods allow the rapid determination of the importance of individual amino acid residues in a polypeptide of interest, and can be applied to polypeptides of unknown structure.

Using the methods discussed above, one of ordinary skill in the art can prepare a variety of polypeptides that are substantially homologous to residues SEQ ID NOs:2, 4, 6, 17, 18, or 19 or allelic variants thereof and retain the ligand-binding properties of the wild-type receptor.

The receptor polypeptides of the present invention, including full-length receptors, receptor fragments (e.g. ligand-binding fragments), and fusion polypeptides can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., *Molecular Cloning: A Laboratory Manual,* 2nd ed., Cold Spring Harbor Laboratory Press, Cold Spring Harbor, N.Y., 1989, and Ausubel et al., ibid.

In general, a DNA sequence encoding a Zcytor5 receptor polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a Zcytor5 receptor polypeptide into the secretory pathway of a host cell, a secretory signal sequence (also known as a leader sequence, prepro sequence or pre sequence) is provided in the expression vector. The secretory signal sequence may be that of the receptor, or may be derived from another secreted protein (e.g., t-PA) or synthesized de novo. The secretory signal sequence is joined to the Zcytor5 DNA sequence in the correct reading frame. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830).

Cultured mammalian cells are preferred hosts within the present invention. Methods for introducing exogenous DNA into mammalian host cells include calcium phosphate-mediated transfection, Wigler et al., *Cell* 14:725 (1978); Corsaro and Pearson, *Somatic Cell Genetics* 7:603 (1981), Graham and Van der Eb, *Virology* 52:456 (1973), electroporation, Neumann et al., *EMBO J.* 1:841–845 (1982), DEAE-dextran mediated transfection, Ausubel et al., eds., *Current Protocols in Molecular Biology* (John Wiley and Sons, Inc., N.Y., 1987), and liposome-mediated transfection, Hawley-Nelson et al., *Focus* 15:73 (1993); Ciccarone et al., *Focus* 15:80 (1993). The production of recombinant polypeptides in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., *J. Gen. Virol.* 36:59–72, (1977) and Chinese hamster ovary (e.g. CHO-K1; ATCC No. CCL 61) cell lines. Additional suitable cell lines are known in the art and available from public depositories such as the American Type Culture Collection, Rockville, Md. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978,) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems may also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g. hygromycin resistance, multi-drug resistance, puromycin acetyltransferase) can also be used.

Other higher eukaryotic cells can also be used as hosts, including insect cells, plant cells and avian cells. Transformation of insect cells and production of foreign polypeptides therein is disclosed by Guarino et al., U.S. Pat. No. 5,162,222; Bang et al., U.S. Pat. No. 4,775,624; and WIPO publication WO 94/06463, which are incorporated herein by reference. The use of *Agrobacterium rhizogenes* as a vector for expressing genes in plant cells has been reviewed by Sinkar et al., *J. Biosci.* (Bangalore) 11:47–58 (1987).

Fungal cells, including yeast cells, and particularly cells of the genus Saccharomyces, can also be used within the present invention, such as for producing receptor fragments or polypeptide fusions. Methods for transforming yeast cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845. Transformed cells are selected by phenotype determined by the selectable marker, commonly drug resistance or the ability to grow in the absence of a particular nutrient (e.g., leucine). A preferred vector system for use in yeast is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936 and 4,661,454. Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii* and *Candida maltosa* are known in the art. See, for example, Gleeson et al., *J. Gen. Microbiol.* 132:3459–3465 (1986) and Cregg, U.S. Pat. No. 4,882,279. Aspergillus cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming Neurospora are disclosed by Lambowitz, U.S. Pat. No. 4,486,533.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell.

Within one aspect of the present invention, a novel receptor is produced by a cultured cell, and the cell is used to screen for ligands for the receptor, including the natural ligand, as well as agonists and antagonists of the natural ligand. To summarize this approach, a cDNA or gene encoding the receptor is combined with other genetic elements required for its expression (e.g., a transcription promoter), and the resulting expression vector is inserted into a host cell. Cells that express the DNA and produce functional receptor are selected and used within a variety of screening systems.

Mammalian cells suitable for use in expressing Zcytor5 receptors and transducing a receptor-mediated signal include cells that express a β-subunit, such as the human $β_c$ subunit. In this regard it is generally preferred to employ a cell that is responsive to other cytokines that bind to receptors in the same subfamily, such as IL-3 or GM-CSF, because such cells will contain the requisite signal transduction pathway(s). It is also preferred to use a cell from the same species as the receptor to be expressed. Within a preferred embodiment, the cell is dependent upon an exogenously supplied hematopoietic growth factor for its proliferation. Preferred cell lines of this type are the human TF-1 cell line (ATCC number CRL-2003) and the AML-193 cell line (ATCC number CRL-9589), which are GM-CSF-dependent human leukemic cell lines. In the alternative, suitable host cells can be engineered to produce a β-subunit (e.g., $b_c$) or other cellular component needed for the desired cellular response. For example, the murine cell line BaF3, Palacios and Steinmetz, *Cell* 41: 727–734 (1985); Mathey-Prevot et al., *Mol. Cell. Biol.* 6: 4133–4135 (1986) or a baby hamster kidney (BHK) cell line can be transfected to express the human $b_c$ subunit (also known as KH97) as well as a Zcytor5 receptor. The latter approach is advantageous because cell lines can be engineered to express receptor subunits from any species, thereby overcoming potential limitations arising from species specificity. In the alternative, species orthologs of the human receptor cDNA can be cloned and used within cell lines from the same species, such as a mouse cDNA in the BaF3 cell line. Cell lines that are dependent upon one hematopoietic growth factor, such as GM-CSF, can thus be engineered to become dependent upon a Zcytor5 ligand.

Cells expressing functional receptor are used within screening assays. A variety of suitable assays are known in the art. These assays are based on the detection of a biological response in a target cell. One such assay is a cell proliferation assay. Cells are cultured in the presence or absence of a test compound, and cell proliferation is detected by, for example, measuring incorporation of tritiated thymidine or by colorimetric assay based on the metabolic breakdown of 3-(4,5-dimethylthiazol-2-yl)-2,5-diphenyl tetrazolium bromide (MTT) (Mosman, *J. Immunol. Meth.* 65: 55–63 (1983). An alternative assay format uses cells that are further engineered to express a reporter gene. The reporter gene is linked to a promoter element that is responsive to the receptor-linked pathway, and the assay detects activation of transcription of the reporter gene. A preferred promoter element in this regard is a serum response element, or SRE, e.g., Shaw et al., *Cell* 56:563–572 (1989). A preferred reporter gene is a luciferase gene, de Wet et al., *Mol. Cell. Biol.* 7:725 (1987). Expression of the luciferase gene is detected by luminescence using methods known in the art (e.g., Baumgartner et al., *J. Biol. Chem.* 269:29094–29101 (1994); Schenborn and Goiffin, *Promega Notes* 41:11 (1993). Luciferase activity assay kits are commercially available from, for example, Promega Corp., Madison, Wis. Target cell lines of this type can be used to screen libraries of chemicals, cell-conditioned culture media, fungal broths, soil samples, water samples, and the like. For example, a bank of cell-conditioned media samples can be assayed on a target cell to identify cells that produce ligand. Positive cells are then used to produce a cDNA library in a mammalian expression vector, which is divided into pools, transfected into host cells, and expressed. Media samples from the transfected cells are then assayed, with subsequent division of pools, re-transfection, subculturing, and re-assay of positive cells to isolate a cloned cDNA encoding the ligand.

A natural ligand for the Zcytor5 receptor can also be identified by mutagenizing a cell line expressing the receptor and culturing it under conditions that select for autocrine growth. See WIPO publication WO 95/21930. Within a typical procedure, BaF3 cells expressing Zcytor5 and human $b_c$ are mutagenized, such as with 2-ethylmethanesulfonate (EMS). The cells are then allowed to recover in the presence of IL-3, then transferred to a culture medium lacking IL-3 and IL-4. Surviving cells are screened for the production of a Zcytor5 ligand, such as by adding soluble receptor to the culture medium or by assaying conditioned media on wild-type BaF3 cells and BaF3 cells expressing the receptor.

An additional screening approach provided by the present invention includes the use of hybrid receptor polypeptides. These hybrid polypeptides fall into two general classes. It is preferred that the second receptor be a hematopoietic cytokine receptor, such as mpl receptor (Souyri et al., *Cell* 63: 1137–1147 (1990). The hybrid receptor will further comprise a transmembrane domain, which may be derived from either receptor. A DNA construct encoding the hybrid receptor is then inserted into a host cell. Cells expressing the hybrid receptor are cultured in the presence of a ligand for the binding domain and assayed for a response. This system provides a means for analyzing signal transduction mediated by Zcytor5 while using readily available ligands. This system can also be used to determine if particular cell lines are capable of responding to signals transduced by Zcytor5.

Cells found to express the ligand are then used to prepare a cDNA library from which the ligand-encoding cDNA can be isolated as disclosed above. The present invention thus provides, in addition to novel receptor polypeptides, methods for cloning polypeptide ligands for the receptors.

Compounds identified as receptor agonists are useful for stimulating proliferation and development of target cells in vitro and in vivo. For example, agonist compounds are useful as components of defined cell culture media, and may be used alone or in combination with other cytokines and hormones to replace serum that is commonly used in cell culture. Agonists are thus useful in specifically promoting the growth and/or development of testis-derived cells in culture. Agonists and antagonists may also prove useful in the study of spermatogenesis and infertility. Antagonists are useful as research reagents for characterizing sites of ligand-receptor interaction. In vivo, receptor agonists may find application in the treatment of male infertility. Antagonists of receptor function may be useful as male contraceptive agents.

The proposed cytokine binding domain of Zcytor5 appears to be closest to the Interleukin-6 β-chain or gp130 (29% identity). The ligand for zcytor5 is probably a member of the Interleukin-6 family of cytokines which at present includes: Interleukins-6, -11, Leukemia Inhibitory Factor, Oncostatin M, Cardiotropin-1 and Ciliary Neurotrophic Factor.

All Zcytor5 cDNAs isolated thus far do not encode a transmembrane domain nor any recognizable cytoplasmic signaling motifs characteristic of the Class I receptors. Structurally, Zcytor5 bears close similarity to α-subunit of the Ciliary neutrophil Factor receptor (CNTF-Rα). It is quite possible Zcytor5 does not have a transmembrane domain form and that the native molecule is phosphatidyl-inositol linked to the cell membrane in a manner similar to CNTF-Rα.

Rebledo et al. (J. Biol. Chem., 272: 4855–4863) provide evidence for the existence of a third component of the Cardiotropin-1 receptor (CT-1R). CT-1R is believed to have a tripartite structure comprised of gp130, gp190(LIV Receptor β) and an uncharacterized 45kDa (CT-1Rα) subunit that appears to be linked to the cell surface through a phosphatidyl-inositol linkage. CT-1Rα appears to be important for increased sensitivity and specificity of the receptor complex to Cardiotropin-1. The data suggests that Zcytor5 is CT-1Rα. Cardiotropin-1 is a member of the Interleukin-6 family in which gp130 and gp190 are members of a tripartite complex is the Ciliary neurotropic Factor receptor. In this receptor complex, CNTF-Rα comprises the third receptor subunit and it mediates specificity and high affinity binding of the ligand complex. These functions are similar to the proposed ones for CT-1Rα. One might then argue on the basis of "symmetry of nature" that CT-1Rα would physically resemble CNTF-Rα and that the close structural similarity of Zcytor5 to CNTF-Rα would make Zcytor5 a possible candidate for the third subunit of CT-1R. Furthermore, the proposed 45 kDa molecular mass of CT-Rα agrees with that of Zcytor5 and the transcripts of CT-1 and Zcytor5 are found in similar tissues. In particular, both transcripts are found in high levels in heart and in skeletal muscles, which is consistent with the observation that ligand and their receptor subunits are often co-expressed in the same tissue.

Cardiotropin-1 was originally cloned by function as a factor involved in cardiac hypertrophy, an adaptive response of heart muscle to an increased work load. Hypertrophy is characterized by reactivation of genes expressed during fetal heart development and by the accumulation of carsomeric proteins. If Zcytor5 proves to be the subunit that is important in the binding and specificity of Cardiotropin-1 to its receptor, Zcytor5 may prove to be a useful therapeutic antagonist to counteract the hypertrophic response to injury. Cardiotropin-1 has also been shown to promote survival of rat dopaminergic neurons in vitro. An agonist-active soluble receptor may potentially be useful in the treatment of neuronal disorders such as Parkinson's disease.

Zcytor5 may also be used within diagnostic systems for the detection of circulating levels of ligand. Within a related embodiment, antibodies or other agents that specifically bind to Zcytor5 can be used to detect circulating receptor polypeptides. Elevated or depressed levels of ligand or receptor polypeptides may be indicative of pathological conditions, including cancer.

Zcytor5 receptor polypeptides can be prepared by expressing a DNA encoding a Zcytor5 polypeptide as described in SEQ ID NO:1, 3 and 5. To direct the export of the receptor domain from the host cell, the receptor DNA is linked to a second DNA segment encoding a secretory peptide. It is believed that amino acid 1–34 or in the alternative amino acid residues 1–30 are secretory peptides of SEQ ID NO:2. For SEQ ID NO: 4, it is believed that residues 1–33 or in the alternative 1–29 are secretory peptides. For the rat sequence, it is believed that amino acid residues 1–40 define a secretory peptide. These peptides are generally cleaved after secretion by a mammalian cell. In the alternative, other secretory peptides could be fused to the Zcytor5 polypeptide, such as the t-PA secretory peptide. To facilitate purification of the secreted receptor domain, a C-terminal extension, such as a poly-histidine tag, substance P, Flag™ peptide (Hopp et al., *Biotechnology* 6:1204–1210 (1988); available from Eastman Kodak Co., New Haven, Conn.) or another polypeptide or protein for which an antibody or other specific binding agent is available, can be fused to the receptor polypeptide.

In an alternative approach, a receptor extracellular domain can be expressed as a fusion with immunoglobulin heavy chain constant regions, typically an $F_c$ fragment, which contains two constant region domains and a hinge region but lacks the variable region. Such fusions are typically secreted as multimeric molecules wherein the Fc portions are disulfide bonded to each other and two receptor polypeptides are arrayed in closed proximity to each other. Fusions of this type can be used to affinity purify the cognate ligand from solution, as an in vitro assay tool, to block signals in vitro by specifically titrating out ligand, and as antagonists in vivo by administering them parenterally to bind circulating ligand and clear it from the circulation. To purify ligand, a Zcytor5-Ig chimera is added to a sample containing the ligand (e.g., cell-conditioned culture media or tissue extracts) under conditions that facilitate receptor-ligand binding (typically near-physiological temperature, pH, and ionic strength). The chimera-ligand complex is then separated by the mixture using protein A, which is immobilized on a solid support (e.g., insoluble resin beads). The ligand is then eluted using conventional chemical techniques, such as with a salt or pH gradient. In the alternative, the chimera itself can be bound to a solid support, with binding and elution carried out as above. The chimeras may be used in vivo to induce infertility. Chimeras with high binding affinity are administered parenterally (e.g., by intramuscular, subcutaneous or intravenous injection). Circulating molecules bind ligand and are cleared from circulation by normal physiological processes. For use in assays, the chimeras are bound to a support via the $F_c$ region and used in an ELISA format.

A preferred assay system employing a ligand-binding receptor fragment uses a commercially available biosensor instrument (BIAcore™, Pharmacia Biosensor, Piscataway, N.J.), wherein the receptor fragment is immobilized onto the surface of a receptor chip. Use of this instrument is disclosed by Karlsson, *J. Immunol. Methods* 145:229–240 (1991) and Cunningham and Wells, *J. Mol. Biol.* 234:554–563 (1993). A receptor fragment is covalently attached, using amine or sulfhydryl chemistry, to dextran fibers that are attached to gold film within the flow cell. A test sample is passed through the cell. If ligand is present in the sample, it will bind to the immobilized receptor polypeptide, causing a change in the refractive index of the medium, which is detected as a change in surface plasmon resonance of the gold film. This system allows the determination of on- and off-rates, from which binding affinity can be calculated, and assessment of stoichiometry of binding.

Ligand-binding receptor polypeptides can also be used within other assay systems known in the art. Such systems include Scatchard analysis for determination of binding affinity, Scatchard, *Ann. NY Acad. Sci.* 51: 660–672 (1949) and calorimetric assays, Cunningham et al., *Science* 253:545–548 (1991); Cunningham et al., *Science* 254:821–825 (1991).

A receptor ligand-binding polypeptide can also be used for purification of ligand. The receptor polypeptide is immobilized on a solid support, such as beads of agarose, cross-linked agarose, glass, cellulosic resins, silica-based resins, polystyrene, cross-linked polyacrylamide, or like materials that are stable under the conditions of use. Methods for linking polypeptides to solid supports are known in the art, and include amine chemistry, cyanogen bromide activation, N-hydroxysuccinimide activation, epoxide activation, sulfhydryl activation, and hydrazide activation. The resulting media will generally be configured in the form of a column, and fluids containing ligand are passed through the column one or more times to allow ligand to bind to the receptor polypeptide. The ligand is then eluted using changes in salt concentration or pH to disrupt ligand-receptor binding.

Zcytor5 polypeptides can also be used to prepare antibodies that specifically bind to Zcytor5 polypeptides. As used herein, the term "antibodies" includes polyclonal antibodies, monoclonal antibodies, antigen-binding fragments thereof such as $F(ab')_2$ and Fab fragments, and the like, including genetically engineered antibodies. Antibodies are defined to be specifically binding if they bind to a Zcytor5 polypeptide with a $K_a$ of greater than or equal to $10^7$/M. The affinity of a monoclonal antibody can be readily determined by one of ordinary skill in the art (see, for example, Scatchard, ibid.).

Zcytor5 polypeptides can also be used to prepare antibodies that specifically bind to Zcytor5 polypeptides. These antibodies can then be used to manufacture anti-idiotypic antibodies. As used herein, the term "antibodies" includes polyclonal antibodies, monoclonal antibodies, antigen-binding fragments thereof such as $F(ab')_2$ and Fab fragments, and the like, including genetically engineered antibodies. Antibodies are defined to be specifically binding if they bind to a Zcytor5 polypeptide with a $K_a$ of greater than or equal to $10^7$/M. The affinity of a monoclonal antibody can be readily determined by one of ordinary skill in the art (see, for example, Scatchard, ibid.).

Methods for preparing polyclonal and monoclonal antibodies are well known in the art (see for example, Sambrook et al., *Molecular Cloning: A Laboratory Manual,* (Second Edition) (Cold Spring Harbor, N.Y., 1989); and Hurrell, J. G. R., Ed., *Monoclonal Hybridoma Antibodies: Techniques and Applications* (CRC Press, Inc., Boca Raton, Fla., 1982). As would be evident to one of ordinary skill in the art, polyclonal antibodies can be generated from a variety of warm-blooded animals such as horses, cows, goats, sheep, dogs, chickens, rabbits, mice, and rats. The immunogenicity of a Zcytor5 polypeptide may be increased through the use of an adjuvant such as Freund's complete or incomplete adjuvant. A variety of assays known to those skilled in the art can be utilized to detect antibodies which specifically bind to Zcytor5 polypeptides. Exemplary assays are described in detail in *Antibodies: A Laboratory Manual,* Harlow and Lane (Eds.), (Cold Spring Harbor Laboratory Press, 1988). Representative examples of such assays include: concurrent immunoelectrophoresis, radio-immunoassays, radio-immunoprecipitations, enzyme-linked immunosorbent assays (ELISA), dot blot assays, inhibition or competition assays, and sandwich assays.

As would be evident to one of ordinary skill in the art, polyclonal antibodies can be generated by inoculating a variety of warm-blooded animals such as horses, cows, goats, sheep, dogs, chickens, rabbits, mice, hamsters, guinea pigs and rats with a Zcytor5 polypeptide or a fragment thereof. The immunogenicity of a Zcytor5 polypeptide may be increased through the use of an adjuvant, such as alum (aluminum hydroxide) or Freund's complete or incomplete adjuvant. Polypeptides useful for immunization also include fusion polypeptides, such as fusions of Zcytor5 or a portion thereof with an immunoglobulin polypeptide or with maltose binding protein. The polypeptide immunogen may be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immunization.

As used herein, the term "antibodies" includes polyclonal antibodies, affinity-purified polyclonal antibodies, monoclonal antibodies, and antigen-binding fragments, such as $F(ab')_2$ and Fab proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced.

Alternative techniques for generating or selecting antibodies useful herein include in vitro exposure of lymphocytes to Zcytor5 protein or peptide, and selection of antibody display libraries in phage or similar vectors (for instance, through use of immobilized or labeled Zcytor5 protein or peptide). Genes encoding polypeptides having potential Zcytor5 polypeptide binding domains can be obtained by screening random peptide libraries displayed on phage (phage display) or on bacteria, such as *E. coli*. Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409; Ladner et al., U.S. Pat. No. 4,946,778; Ladner et al., U.S. Pat. No. 5,403,484 and Ladner et al., U.S. Pat. No. 5,571,698) and random peptide display libraries and kits for screening such libraries are available commercially, for instance from Clontech (Palo Alto, Calif.), Invitrogen Inc. (San Diego, Calif.), New England Biolabs, Inc. (Beverly, Mass.) and Pharmacia LKB Biotechnology Inc. (Piscataway, N.J.). Random peptide display libraries can be screened using the Zcytor5 sequences disclosed herein to identify proteins which bind to Zcytor. These "binding proteins" which interact with Zcytor5 polypeptides can be used for tagging cells; for isolating homolog polypeptides by affinity purification; they can be directly or indirectly conjugated to drugs, toxins, radionuclides and the like. These binding proteins can also be used in analytical methods such as for screening expression libraries and neutralizing activity. The binding proteins can also be used for diagnostic assays for determining circulating levels of polypeptides; for detecting or quantitating soluble polypeptides as marker of underlying pathology or disease. These binding proteins can also act as Zcytor5 "antagonists" to block Zcytor5 binding and signal transduction in vitro and in vivo.

Antibodies can also be generated gene therapy. The animal is administered the DNA or RNA which encodes Zcytor5 or an immunogenic fragment thereof so that cells of the animals are transfected with the nucleic acid and express the protein which in turn elicits an immunogenic response. Antibodies which then are produced by the animal are isolated in the form of polyclonal or monoclonal antibodies.

Antibodies to Zcytor5 may be used for tagging cells that express the protein, for affinity purification, within diagnostic assays for determining circulating levels of soluble protein polypeptides, and as antagonists to block ligand binding and signal transduction in vitro and in vivo.

Methods for preparing polyclonal and monoclonal antibodies are well known in the art (see for example, Sambrook et al., *Molecular Cloning: A Laboratory Manual,* Second Edition, Cold Spring Harbor, N.Y. (1989); and Hurrell, J. G. R., Ed., *Monoclonal Hybridoma Antibodies: Techniques and Applications* (CRC Press, Inc., Boca Raton, Fla., 1982). As would be evident to one of ordinary skill in the art, polyclonal antibodies can be generated from a variety of warm-blooded animals such as horses, cows, goats, sheep, dogs, chickens, rabbits, mice, and rats. Generally speaking, antibodies against which bind to the claimed Zcytor5 polypeptides can be raised by immunization of animals with a Zcytor5 polypeptide or a fragment thereof. The immunogenicity of a Zcytor5 polypeptide may be increased through the use of an adjuvant such as Freund's complete or incomplete adjuvant. A variety of assays known to those skilled in the art can be utilized to detect antibodies which specifically bind to Zcytor5 polypeptides. Exemplary assays are described in detail in *Antibodies: A Laboratory Manual,* Harlow and Lane (Eds.) (Cold Spring Harbor Laboratory Press, 1988). Representative examples of such assays include: concurrent immunoelectrophoresis, radio-immunoassays, radio-immunoprecipitations, enzyme-linked immunosorbent assays (ELISA), dot blot assays, inhibition or competition assays, and sandwich assays.

Antibodies to Zcytor5 are may be used for tagging cells that express the receptor, for affinity purification, within diagnostic assays for determining circulating levels of soluble receptor polypeptides, and as antagonists to block ligand binding and signal transduction in vitro and in vivo.

Uses

The tissue specificity of Zcytor5 expression suggests that Zcytor5 may be a receptor for growth and/or maintenance factor in the thyroid heart and skeletal muscle. Zcytor5 could therefor be used to down regulate the effects of the factor by administering soluble Zcytor5 to the patient. For example the soluble receptor could be used to lessen the effect of cardiotrophin-1 on cardiac pathologies. Thus preventing enlargement of the heart due to heart disease. Zcytor5 could also be used as a diagnostic to test for the presence of cardiotrophin-1 in the blood. Furthermore, Zcytor5 can be used to discover other possible ligands which would bind to Zcytor5.

The present invention also provides reagents which will find use in diagnostic applications. For example, the Zcytor5 gene. A probe comprising the Zcytor5 DNA or RNA or a subsequence thereof can be used to determine if the Zcytor5 gene is present on chromosome 1 or if a mutation has occurred.

Antibodies to Zcytor5 could be used to purify Zcytor5 and as a therapeutic to modulate the effect of the Zcytor5 ligand. The anti-idiotypic antibody to Zcytor5 could be used to purify the ligand of Zcytor5 and the administration of the anti-idiotypic antibody could be used to modulate the effect of the Zcytor5 ligand.

The invention is further illustrated by the following non-limiting examples.

EXAMPLE 1

Cloning of Human Zcytor5

Human Zcytor5 was identified from expressed sequence tag (EST) 698365 (SEQ ID NO: 7) identified in an EST database. The cDNA containing EST 698365 was obtained from Incyte Pharmaceuticals, Inc. as dried DNA. Upon reconstitution in water, the cDNA was transfected into *E. coli* strain DH10B. The plasmid was designated pSL8365. The EST in plasmid pSL8365 was sequenced, revealing an insert of 952 bp.

The GENE TRAPPER® cDNA positive selection system (Life Technologies, Gaithersburg, Md.) employing oligonucleotide ZC11,286 (SEQ ID NO: 8) was used to isolate the plasmid Hzcytor5-9 from a human lung cDNA library (obtained from Life Technologies Inc., Gaithersburg, Md.) in accordance with the manufacturer's directions. Hzcytor5-9 extended the sequence of pSL8365 by 459 bp. The sequence present in Hzcytor5-9 allowed the isolation of an overlapping EST No. 485212 (SEQ ID NO: 9), which extended the open reading frame of Hzcytor5-9 by a further 33 codons.

A cDNA encoding full-length Zcytor5 was isolated from a human testis cDNA library. (See Example 2 for the preparation of the human cDNA testis library.) The library was comprised of eighty pools of plasmid DNA, each pool comprised of 10,000 independent recombinants. The presence of Zcytor5 cDNA in each library pool was determined by PCR employing primers ZC11,663 (SEQ ID NO: 10) and ZC12,212 (SEQ ID NO: 11). PCR was carried out using AMPLITAQ® DNA polymerase (Perkin-Elmer) in buffer conditions recommended by the supplier. The amplification was carried out at 940° C. for 1 minute followed by 30 cycles, each cycle consisting of 20 seconds at 94° C., 1 minute at 66° C. and 7 minutes at 74° C. Five cDNA pools were found to be positive for the 420 bp PCR product by agarose gel electrophoresis.

Plasmid DNA from one positive library pool was electrophoresed into DH10B cells and plated. Colony lifts were prepared using Hybond-N filters (Amersham; Arlington Heights, Ill.) according to the procedure provided by the manufacturer. Following denaturation and neutralization, DNA was cross-linked onto the filters with 1,200 μJoules of UV energy in a STRATALINKER® (Stratagene Cloning Systems). Cell debris was removed by several washes in 0.25×standard sodium citrate (SSC), 0.25 sodium dodecyl sulfate (SDS) and 1 mM EDTA at 65° C. The filters were then pre-hybridized overnight at 65° C. in EXPRESSHYB® solution (Clontech) with 1 mg/ml heat denatured salmon sperm DNA. Colonies positive for Zcytor5 were identified by hybridization with a probe that was generated from EST 484212 (SEQ ID NO: 9) cDNA employing PCR primers ZC11,663 (SEQ ID NO: 10) and ZC12,212 (SEQ ID NO: 11). The PCR product probe was purified by agarose gel electrophoresis. 100 ng of the probe was labeled with $^{32}$P dCTP using the MULTI-PRIME® DNA labeling system (Amersham). Unincorporated label was removed with a NUCTRAP® column (Stratagene). Probe hybridization was carried out overnight at 65° C. in EXPRESSHYB® solution at a probe concentration of 1×10$^6$ cpm/ml. The filters were washed at 65° C. in a wash buffer containing 0.25×SSC, 0.25 SDS and 1 mM EDTA.

Three positive signals were identified and were subjected to colony purification via a second round of filter hybridization. Sequence analysis of one positive clone, SEQ ID NO: 3 was found to be full length human Zcytor-5. Sequencing of a several overlapping clones revealed a second full-length sequence SEQ ID NO: 1 which is an allelic variant of SEQ ID NO: 3.

Example 2
Construction of the Human Testis cDNA Library

Fourteen μl of poly d(T)-selected poly (A)$^+$ human testis mRNA (Clontech) at a concentration of 1.0 μg/μl was mixed with 2 μl of 20 pmole/μl first strand primer ZC2938 (SEQ ID NO: 12) containing an Sst I restriction site. The mixture was heated at 65° C. for 4 minutes and cooled by chilling on ice. First strand cDNA synthesis was initiated by the addition of 8 μl of 250 mM Tris-HCl, pH 8.3, 375 mM KCl, 15 mM MgCl$_2$ (5×SUPERSCRIPT™ buffer; GIBCO BRL), 4 μl of 100 mM dithiothreitol (DTT) and 2 μl of a deoxynucleotide triphosphate solution containing 10 mM each of dATP, dGTP, dTTP and 5-methyl-dCTP (Pharmacia LKB Biotechnology Inc.) to the RNA-primer mixture. The reaction mixture was incubated at 45° C. for 4 minutes followed by the addition of 10 μl of 200 U/μl RNase H$^-$ reverse transcriptase (GIBCO BRL). The efficiency of the first strand synthesis was analyzed in a parallel reaction by the addition of 10 μCi of $^{32}$P-αdCTP to a 10 μl aliquot of the reaction mixture to label the reaction for analysis. The reactions were incubated at 45° C. for 1 hour followed by an incubation at 50° C. for 15 minutes. Unincorporated $^{32}$P-αdCTP in the labeled reaction was removed by chromatography on a 400 pore size gel filtration column (CHROMA SPIN+TE-400™; Clontech Laboratories Inc.). Unincorporated nucleotides in the unlabeled first strand reaction were removed by twice precipitating the cDNA in the presence of 10 μg of glycogen carrier, 2.5 M ammonium acetate and 2.5 volume ethanol. The unlabeled cDNA was resuspended in 50 μl water for use in second strand synthesis. The length of the labeled first strand cDNA was determined by agarose gel electrophoresis.

Second strand synthesis was performed on first strand cDNA under conditions that promoted first strand priming of second strand synthesis resulting in DNA hairpin formation. The reaction mixture was assembled at room temperature and was comprised of 66 μl of the unlabeled first strand cDNA, 20 μl of 5×polymerase I buffer (100 mM Tris: HCl, pH 7.4, 500 mM KCl, 25 mM MgCl$_2$, 50 mM (NH$_4$)$_2$SO$_4$), 1 μl of 100 mM DTT, 1 μl of a solution containing 20 mM of each deoxynucleotide triphosphate, 3 μl of 5 mM β-NAD, 1 μl of 4 U/μl of E. coli DNA ligase (New England Biolabs Inc., Beverly, Mass.) and 5 μl of 10 U/μl E. coli DNA polymerase I (New England Biolabs, Inc.). The reaction was incubated at room temperature for 5 minutes followed by the addition of 2 μl of 2.2 U/μl RNase H (GIBCO BRL). A parallel reaction in which a 10 μl aliquot of the second strand synthesis mixture was labeled by the addition of 10 μCi $^{32}$P-αdCTP was used to monitor the efficiency of second strand synthesis. The reactions were incubated at 15° C. for two hours followed by a 15 minute incubation at room temperature. Unincorporated $^{32}$P-αdCTP in the labeled reaction was removed by chromatography through a 400 pore size gel filtration column (Clontech Laboratories, Inc.) before analysis by agarose gel electrophoresis. The unlabeled reaction was terminated by two extractions with phenol/chloroform and a chloroform extraction followed by ethanol precipitation in the presence of 2.5 M ammonium acetate.

The single-stranded DNA of the hairpin structure was cleaved using mung bean nuclease. The reaction mixture contained 100 μl of second strand cDNA, 20μl of 10×mung bean nuclease buffer (Stratagene Cloning Systems, La Jolla, Calif.), 16 μl of 100 mM DTT, 51.5 μl of water and 12.5 μl of a 1:10 dilution of mung bean nuclease (Promega Corp.; final concentration 10.5 U/μl) in mung bean nuclease dilution buffer. The reaction was incubated at 37° C. for 15 minutes. The reaction was terminated by the addition of 20 μl of 1 M Tris: HCl, pH 8.0 followed by sequential phenol/chloroform and chloroform extractions as described above. Following the extractions, the DNA was precipitated in ethanol and resuspended in water.

The resuspended cDNA was blunt-ended with T4 DNA polymerase. The cDNA, which was resuspended in 138 μl of water, was mixed with 40 μl of 5×T4 DNA polymerase buffer (250 mM Tris: HCl, pH 8.0, 250 mM KCl, 25 mM MgCl$_2$), 3 μl 0.1 M DTT, 5 μl of a solution containing 10 mM of each deoxynucleotide triphosphate and 4 μl of 1 U/μl T4 DNA polymerase (Boehringer Mannheim Corp., Indianapolis, Ind.). After incubation of 1 hour at 10° C., the reaction was terminated by the addition of 10 µl of 0.5 M EDTA followed by serial phenol/chloroform and chloroform extractions as described above. The DNA was chromatographed through a 400 pore size gel filtration column (Clontech Laboratories Inc. Palo Alto, Calif.) to remove trace levels of protein and to remove short cDNAs less than about 400 bp in length. The DNA was ethanol precipitated in the presence of 12 µg glycogen carrier and 2.5 M ammonium acetate and was resuspended in 10 µl of water. Based on the incorporation of $^{32}$P-αdCTP, the yield of cDNA was estimated to be about 2 µg from a starting template of 12.5 µg.

Eco RI adapters were ligated onto the 5' ends of the cDNA to enable cloning into a lambda phage vector. A 10 µl aliquot of cDNA (containing about 2 µg of cDNA) and 11 µl of 65 pmole/µl of Eco RI adapter (Pharmacia LKB Biotechnology Inc.) were mixed with 3 µl 10×ligase buffer (Promega Corp.), 3 µl 10 mM ATP and 3 µl of 15 U/µl T4 DNA ligase (Promega Corp.). The reaction was incubated overnight (about 18 hours) at 12.5° C. The reaction was terminated by the addition of 150 µl of water and 10 µl of 3 M Na acetate, followed by incubation at 65° C. for 30 minutes. After incubation, the cDNA was extracted with phenol/chloroform and chloroform as described above and precipitated in the presence of 2.5 M ammonium acetate and 1.2 volume of isopropanol. Following centrifugation, the cDNA pellet was washed with 70% ethanol, air dried and resuspended in 89 µl water.

To facilitate the directional cloning of the cDNA into a lambda phage vector, the cDNA was digested with Sst-I resulting in a cDNA having 5' Eco RI and 3' Sst-I cohesive ends. The Sst-I restriction site at the 3' end of the cDNA had been previously introduced through primer ZC2938 (SEQ ID NO: 12). Restriction enzyme digestion was carried out in a reaction containing 89 µl of cDNA described above, 10 µl of 6 mM Tris: HCl, 6 mM MgCl$_2$, 150 mM NaCl, 1 mM DTT (10×D buffer; Promega Corp., Madison, Wis.) and 1 µl of 12 U/µl Not I (Promega Corp.). Digestion was carried out at 37° C. for 1 hour. The reaction was terminated by serial phenol/chloroform and chloroform extractions. The cDNA was ethanol precipitated, washed with 70% ethanol, air dried and resuspended in 20 µl of 1×gel loading buffer (10 mM Tris: HCl, pH 8.0, 1 mM EDTA, 5% glycerol and 0.125% bromphenol blue).

The resuspended cDNA was heated to 65° C. for 5 minutes, cooled on ice and electrophoresed on a 0.8% low melt agarose gel (SEA PLAQUE GTG™ low melt agarose; FMC Corp.). Unincorporated adapters and cDNA below 1.6 kb in length were excised from the gel. The electrodes were reversed, and the cDNA was electrophoresed until concentrated near the lane of origin. The area of the gel containing the concentrated cDNA was excised and placed in a microfuge tube, and the approximate volume of the gel slice was determined. A 300 µl aliquot of water, approximately three times the volume of the gel slice, was added to the tube. The agarose was then melted by heating to 65° C. for 15 minutes. Following equilibration of the sample to 42° C., 10 µl of 1 U/µl β-agarose I (New England Biolabs, Inc.) was added, and the mixture was incubated for 90 minutes to digest the agarose. After incubation, 40 µl of 3 M Na acetate was added to the sample, and the mixture was incubated on ice for 15 minutes. The sample was centrifuged at 14,000×g for 15 minutes at room temperature to remove undigested agarose. The cDNA in the supernatant was ethanol precipitated, washed in 70% ethanol, air-dried and resuspended in 37 µl of water for the kinase reaction to phosphorylate the ligated Eco RI adapters.

To the 37 µl cDNA solution described above was added 10 µl of 10×ligase buffer (Stratagene Cloning Systems), and the mixture was heated to 65° C. for 5 minutes. The mixture was cooled on ice, and 5 µl of 10 mM ATP and 3 µl of 10 U/µl of T4 polynucleotide kinase (Stratagene Cloning Systems) were added. The reaction was incubated at 37° C. for 45 minutes and was terminated by heating to 65° C. for 10 minutes followed by serial extractions with phenol/chloroform and chloroform. The phosphorylated cDNA was ethanol precipitated in the presence of 2.5 M ammonium acetate, washed with 70% ethanol, air dried and resuspended in 12.5 µl water. The concentration of the phosphorylated cDNA was estimated to be about 40 fmole/µl.

EXAMPLE 3
Northern Blot Analysis of Human Zcytor5

A 300 bp double stranded DNA probe for Northern analysis was prepared from pSL1034 by PCR using oligonucleotide primers ZC 10,787 (SEQ ID NO:13) and ZC 11,097 (SEQ ID NO:14). The 300 bp PCR fragment was gel-purified using a QIAQUICK® purification kit (Qiagen Inc., Chatsworth, Calif.) and random-primer labeled using a MULTIPRIME® kit (Amersham Corp.). Labeled cDNA was purified from free counts using a Stratagene push column. Human multiple tissue Northern blots (Clontech Laboratories) and a human fetal tissue Northern blot (Clontech Laboratories) were pre-hybridized for three hours at 68° C. using EXPRESSHYB hybridization solution (Clontech Laboratories). The $^{32}$P-labeled cDNA probe was then added to 10 mls of fresh hybridization solution at 10$^6$ cpm/ml overnight at 68° C. The blots were washed several times at room temperature in wash solution containing 2×SSC, 0.05% SDS, then with continuous agitation for 40 min at room temperature. The blots were then washed in 0.1×SSC, 0.1% SDS at 50° C. for 40 min with one change of wash solution.

A single transcript of ~2.3 kb was detected after exposure to film. In the multiple tissue blots (MTN, MTN II and MTN III; Clontech Laboratories) the transcript was present in highest abundance in placenta, thyroid, heart and skeletal muscle with lower levels in prostate and trachea. Trace mRNA levels were found in kidney, pancreas, testis, small intestine, colon, lymph node, adrenal cortex and bone marrow.

EXAMPLE 4
Chromosomal Assignment and Placement of Human Zcytor-5

Zcytor5 was mapped to chromosome 19 using the commercially available version of the "Stanford G3 Radiation Hybrid Mapping Panel" (Research Genetics, Inc., Huntsville, Ala.). The "Stanford G3 RH Panel" contains PCRable DNAs from each of 83 radiation hybrid clones of the whole human genome, plus two control DNAs (the RM donor and the A3 recipient).

For the mapping of Zcytor5 with the "Stanford G3 RH Panel", 20 µl reactions were set up in a PCRable 96-well microtiter plate (Stratagene, La Jolla, Calif.) and used in a "RoboCycler Gradient 96" thermal cycler (Stratagene). Each of the 85 PCR reactions consisted of 2 µl 10×KlenTaq PCR reaction buffer (CLONTECH Laboratories, Inc., Palo Alto, Calif.), 1.6 µl dNTPs mix (2.5 mM each, PERKIN-ELMER, Foster City, Calif.), 1 µl sense primer, (SEQ ID NO:13) 5' TAT GGC CAG GAC AAC ACA 3', 1 µl antisense primer, (SEQ ID NO:14), 5' ATA GGG CGT AAA GAG AGC 3', 2 µl "RediLoad" (Research Genetics, Inc., Huntsville, Ala.), 0.4 µl 50×Advantage KlenTaq Polymerase Mix (Clontech Laboratories, Inc.), 25 ng of DNA from an individual hybrid clone or control and x μl ddH20 for a total volume of 20 μl. The reactions were overlaid with an equal amount of mineral oil and sealed. The PCR cycler conditions were as follows: an initial 1 cycle 5 minute denaturation at 95° C., 35 cycles of a 1 minute denaturation at 95° C., 1 minute annealing at 66° C. and 1.5 minute extension at 72° C., followed by a final 1 cycle extension of 7 minutes at 72° C. The reactions were separated by electrophoresis on a 2% agarose gel (Life Technologies, Gaithersburg, Md.).

The results showed linkage of Zcytor5 to the framework marker WI-7289 with a LOD score of >10 and at a distance of 14.67 cR_10000 from the marker. The use of surrounding markers positions Zcytor5 in the 19p13.1-p11 region on the integrated LDB chromosome 19 map.

EXAMPLE 5
Cloning of the Rat Zcytor5 Gene

Rat Zcytor5 cDNA encoding Zcytor5 was isolated from an amplified Rat testis cDNA library with a probe that was generated by primers ZC12212 (SEQ ID NO: 11) and ZC10785 (SEQ ID NO:15) and 10 ng of plasmid pSL85212 as a template obtained from cDNA containing EST 698365 as described in Example 1. The probe was prepared by PCR by combining 1 μl containing 10 ng of pSL85212, 1 μl of ZC12212 having a concentration of 20 pmole/μl, 1 μl of ZC10785 having a concentration of 20 pmole/μl, 0.5 μl of dNTP having a concentration of 20 mM of DATP, dGTP, dCTP and dTTP, 5 μl of 10×Klentaq polymerase buffer (Clontech) 5 μl Klentaq DNA polymerase (Clontech) and 39.5 μl water. The amplification was carried out at 94° C. for 1 minute followed by 30 cycles, each cycle consisting of 15 seconds at 95° C., 20 seconds at 62° C. and 1 minutes at 68° C. The reaction had a final incubation at 68° C. for 10 minutes.

The resulting PCR product was diluted 1:100 with water. Four μl of the diluted PCR product was re-amplified using the above-described conditions and the resultant PCR product was further purified by electrophoresis on low-melt agarose gel. The DNA probe was recovered from low-melt gel by digestion with β-Agarose I digestion. The rat Zcytor5 gene was then cloned from a rat testis library which was constructed as described below in Example 6.

In cloning the rat Zcytor5 gene, the library was first amplified by plating 3.10⁶ plaque forming units (pfu) from the previously constructed primary library onto 98 150 mm NZY plates. Ten ml of serum medium was added to each plate and was incubated for several hours at room temperature. Following incubation, the phage lysates were collected and pooled to yield the amplified phage library.

1.5 million pfus from the amplified rat testis cDNA library were plated onto 150 mm NZY plates at a density of 40,000 pfu/plate on XL-1 Blue MRF' host cells. Following incubation at 37° C. overnight, filter lifts were made using HYBOND-N™ membranes (Amersham), according to the procedures provided by the manufacturer. The filters were processed by denaturation in solution containing 1.5 M NaCl and 0.5 M NaOH for 8 minutes at room temperature. The filters were neutralized in 0.5 M Tris: HCl, pH 7.2 for 5 minutes. Phage DNA was fixed onto the filters with 1,200 μJoules of UV energy in a UV Cross-linker (Stratagene). The filters were then washed with 0.25×SSC at 70° C. to remove excess cellular debris. Filter pre-hybridization was carried out in a hybridization solution containing 5×SSC, 5×Denhardt solution, 0.2% SDS, 1 mM EDTA and heat denatured sheared salmon-sperm DNA at a final concentration of 100 μg/ml for 72 hours at 60° C.

75 ng of probe DNA was labeled with $^{32}$P-dCTP using a MEGAPRIME® labeling kit (Amersham) and was purified with a NUCTRAP® column (Stratagene). The labeled probe was heat-denatured and added to fresh hybridization solution at a concentration of $1.5 \times 10^6$ cpm/ml. Into this solution were also added the filters containing the phage particles. Hybridization of the probes to the phage-containing filters was completed overnight at 45° C. Following hybridization, the filters were washed in a solution containing 0.25×SSC, 0.25% SDS and 1 mM EDTA at 50° C. The washed filters were autoradiographed for 72 hours at −70° C. with intensifying screens. Examination of the autoradiographs revealed multiple regions that hybridized with the labeled probe. Agar plugs were picked from 56 regions for plaque purification. Of the positive signals, eleven produce positive phagemids following secondary and tertiary hybridization screens. The plasmids within the positive phagemids were recovered using the EXASSIT/SOLR™ system according to the manufacturer's specifications. A clone designated pSLRatR5-1 was sequenced and found to encode full length Rat Zcytor5 (SEQ ID NO: 5)

EXAMPLE 6
Production of Rat Testis cDNA Library

The rat first strand cDNA reaction contained 10 μl of rat testis poly d(T)-selected poly (A)⁺ mRNA (Clontech, Palo Alto, Calif.) at a concentration of 1.0 μg/μl, and 2 μl of 20 pmole/μl first strand primer ZC6091 (SEQ ID NO: 16) containing an Xho I restriction site. The mixture was heated at 70° C. for 4 minutes and cooled by chilling on ice. First strand cDNA synthesis was initiated by the addition of 8 μl of first strand buffer (5× SUPERSCRIPT™ buffer; Life Technologies, Gaithersburg, Md.), 4 μl of 100 mM dithiothreitol, and 2 μl of a deoxynucleotide triphosphate solution containing 10 mM each of DATP, dGTP and 5-methyl-dCTP (Pharmacia LKB Biotechnology, Piscataway, N.J.) to the RNA-primer mixture. The reaction mixture was incubated at 45° C. for 2 minutes, followed by the addition of 10 μl of 200 U/μl RNase H-reverse transcriptase (SUPERSCRIPT II®; Life Technologies). The efficiency of the first strand synthesis was analyzed in a parallel reaction by the addition of 10 μCi of $^{32}$P-αdCTP to 5 μl aliquot from one of the reaction mixtures to label the reaction for analysis. The reactions were incubated at 45° C. for 1 hour followed by an incubation at 50° C. for 10 minutes. Unincorporated $^{32}$P-αdCTP in the labeled reaction was removed by chromatography on a 400 pore size gel filtration column (Clontech). The unincorporated nucleotides and primers in the unlabeled first strand retains were removed by chromatography on 400 pore size gel filtration column (Clontech). The length of labeled first strand cDNA was determined by agarose gel electrophoresis.

The second strand reaction contained 102 μl of the unlabeled first strand cDNA, 30 μl of 5×polymerase I buffer (125 mM Tris: HCl, pH 7.5, 500 mM KCl, 25 mM MgCl₂, 50 mM (NH₄)₂SO₄)), 2 μl of 100 mM dithiothreitol, 3 μl of a solution containing 10 mM of each deoxynucleotide triphosphate, 5 μl of 5 mM β-NAD, 2 μl of 3 U/μl E. coli DNA ligase (New England Biolabs), 5 μl of 10 U/μl E. coli DNA polymerase I (New England Biolabs), and 1.5 μl of 2 U/μl RNase H (Life Technologies). A 10 μl aliquot from one of the second strand synthesis reactions was labeled by the addition of 10 μCi $^{32}$P-αdCTP to monitor the efficiency of second strand synthesis. The reactions were incubated at 16° C. for two hours, followed by the addition of 10 μl T4 DNA polymerase (10 U/μl, Boerhinger Mannheim) and incubated for an additional 5 minutes at 16° C. Unincorporated $^{32}$P-αdCTP in the labeled reaction was removed by chromatography through a 400 pore size gel filtration column (Clontech) before analysis by agarose gel electrophoresis.

The unlabeled was terminated by the addition of 20 µl 0.5 EDTA and extraction with phenol/chloroform and chloroform followed by ethanol precipitation in the presence of 2.5 M ammonium acetate. The yield of cDNA was estimated to be approximately 2 µg from starting mRNA template of 10 µg.

Eco RI adapters were ligated onto the 5' ends of the cDNA described above to enable cloning into an expression vector. A 10.5 µl aliquot of cDNA (~2 µg) and 5 µl of 65 pmole/µl of Eco RI adapter (Pharmacia LKB Biotechnology Inc.) were mixed with 2.5 µl 10×ligase buffer 66 mM Tris-HCl pH 7.5, 10 mM MgCl$_2$, 2.5 µl of 10 mM ATP and 1 µl of 15 U/µl T4 DNA ligase (Promega Corp., Madison, Wis.). The reaction was incubated overnight (~12 hours) at 12° C. The reaction was terminated by incubation at 70° C. for 20 minutes. After incubation, the reaction was cooled to 37° C. To the reaction was added 2.5 µl 10 mM ATP and 3 µl 10 U/µl T4 polynucleotide kinase (Life Technologies) to phosphorylate the ligated Eco RI adapters.

To facilitate the directional cloning of the cDNA into an expression vector, the cDNA was digested with Xho I, resulting in a cDNA having a 5' Eco RI cohesive end and a 3' Xho I cohesive end. The Xho I restriction site at the 3' end of the cDNA had been previously introduced using the ZC6091 primer (SEQ ID NO: 3). Restriction enzyme digestion was carried out in a reaction mixture containing 25 µl of cDNA described above, 15 µl of 10×H Buffer (Boehringer Mannheim), 109 µl H$_2$O, and 1.0 µl of 40 U/µl Xho I (Boehringer Mannheim). Digestion was carried out at 37° C. for 40 minutes. The reaction was terminated by incubation at 65° C. for 10 minutes and chromatography through a 400 pore size gel filtration column (Clontech).

The cDNA was ethanol precipitated, washed with 70% ethanol, air dried and resuspended in 20 µl of 1×gel loading buffer (10 mM Tris:HCl, pH 8.0, 1 mM EDTA, 5% glycerol and 0.125% bromphenol blue). The resuspended cDNA was heated to 65° C. for 5 minutes, cooled on ice and electrophoresed on a 0.8% low melt agarose gel. The contaminating adapters and cDNA below 0.6 Kb in length were excised from the gel. The electrodes were reversed, and the cDNA was electrophoresed until concentrated near the lane origin. The area of the gel containing the concentrated cDNA was excised and placed in a microfuge tube, and the approximate volume of the gel slice was determined. An aliquot of water approximately three times the volume of the gel slice (300 µl) and 35 µl 10×β-agarose I buffer (New England Biolabs) was added to the tube, and the agarose was melted by heating to 65° C. for 15 minutes. Following equilibration of the sample to 45° C., 3 µl of 1 U/µl β-agarose I (New England Biolabs) was added, and the mixture was incubated for 60 minutes at 45° C. to digest the agarose. After incubation, 40 µl of 3 M Na acetate was added to the sample, and the mixture was incubated on ice for 15 minutes. The sample was centrifuged at 14,000×g for 15 minutes at room temperature to remove undigested agarose. The cDNA was ethanol precipitated, washed in 70% ethanol, air-dried and resuspended in 10 µl water.

The resulting cDNA was cloned into the lambda phage vector λZapII that was predigested with Eco RI and Xho I and dephosphorylated (Stratagene Cloning Systems, La Jolla, Calif.). Ligation of the cDNA to the λZapII vector was carried out in a reaction mixture containing 1.0 µl of prepared vector, 1.0 µl of rat testis cDNA, 1.0 µl 10×Ligase Buffer (Promega), 1.0 µl of 10 mM ATP, 5 µl water, and 1.0 µl of T4 DNA Ligase at 15 units/ml (Promega). The ligation mixture was incubated at 5° C.–15° C. overnight in a temperature gradient. After incubation, the ligation mixture was packaged into phage using GIGPACK III GOLD packaging extract (Stratagene Cloning Systems) and the resulting library was titered according to the manufacturer's specifications.

We claim:

1. An isolated polypeptide comprised of an amino acid sequence selected from the group consisting of SEQ ID NO: 2, SEQ ID NO:4, SEQ ID NO:6, and SEQ ID NOs: 17–34 and 37.

2. An isolated peptide or polypeptide which has an amino acid sequence of an epitope-bearing portion of the Zcytor5 polypeptide, wherein the amino acid sequence of said epitope-bearing portion of Zcytor5 is comprised of a polypeptide selected from the group consisting of SEQ ID NO's: 32–34 and 37.

* * * * *

SEQUENCE LISTING (1) GENERAL INFORMATION:

(iii) NUMBER OF SEQUENCES: 37

(2) INFORMATION FOR SEQ ID NO:1:

(i) SEQUENCE CHARACTERISTICS:
      (A) LENGTH: 1690 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: Coding Sequence
      (B) LOCATION: 52...1317
      (D) OTHER INFORMATION:

(xi) SEQUENCE DESCRIPTION: SEQ ID NO:1:

```
CGCCACGCGC CGAGCCGCAG CCCGCCGCGC GCCCCCGGCA GCGCCGGCCC C ATG CCC         57
                                                          Met Pro
                                                           1

GCC GGC CGC CGG GGC CCC GCC GCC CAA TCC GCG CGG CGG CCG CCG CCG        105
Ala Gly Arg Arg Gly Pro Ala Ala Gln Ser Ala Arg Arg Pro Pro Pro
          5               10                  15
```

| | | |
|---|---|---|
| TTG CTG CCC CTG CTG CTG CTG CTC TGC GTC CTC GGG GCG CCG CGA GCC<br>Leu Leu Pro Leu Leu Leu Leu Leu Cys Val Leu Gly Ala Pro Arg Ala<br>20                         25                  30 | | 153 |
| GGA TCA GGA GCC CAC ACA GCT GTG ATC AGT CCC CAG GAT CCC ACG CTT<br>Gly Ser Gly Ala His Thr Ala Val Ile Ser Pro Gln Asp Pro Thr Leu<br>35                        40                     45                  50 | | 201 |
| CTC ATC GGC TCC TCC CTG CTG GCC ACC TGC TCA GTG CAC GGA GAC CCA<br>Leu Ile Gly Ser Ser Leu Leu Ala Thr Cys Ser Val His Gly Asp Pro<br>              55                     60                     65 | | 249 |
| CCA GGA GCC ACC GCC GAG GGC CTC TAC TGG ACC CTC AAT GGG CGC CGC<br>Pro Gly Ala Thr Ala Glu Gly Leu Tyr Trp Thr Leu Asn Gly Arg Arg<br>                  70                     75                    80 | | 297 |
| CTG CCC CCT GAG CTC TCC CGT GTA CTC AAC GCC TCC ACC TTG GCT CTG<br>Leu Pro Pro Glu Leu Ser Arg Val Leu Asn Ala Ser Thr Leu Ala Leu<br>          85                     90                     95 | | 345 |
| GCC CTG GCC AAC CTC AAT GGG TCC AGG CAG CGG TCG GGG GAC AAC CTC<br>Ala Leu Ala Asn Leu Asn Gly Ser Arg Gln Arg Ser Gly Asp Asn Leu<br>         100                    105               110 | | 393 |
| GTG TGC CAC GCC CGT GAC GGC AGC ATC CTG GCT GGC TCC TGC CTC TAT<br>Val Cys His Ala Arg Asp Gly Ser Ile Leu Ala Gly Ser Cys Leu Tyr<br>115                     120                   125               130 | | 441 |
| GTT GGC CTG CCC CCA GAG AAA CCC GTC AAC ATC AGC TGC TGG TCC AAG<br>Val Gly Leu Pro Pro Glu Lys Pro Val Asn Ile Ser Cys Trp Ser Lys<br>               135                   140               145 | | 489 |
| AAC ATG AAG GAC TTG ACC TGC CGC TGG ACG CCA GGG GCC CAC GGG GAG<br>Asn Met Lys Asp Leu Thr Cys Arg Trp Thr Pro Gly Ala His Gly Glu<br>        150                    155               160 | | 537 |
| ACC TTC CTC CAC ACC AAC TAC TCC CTC AAG TAC AAG CTT AGG TGG TAT<br>Thr Phe Leu His Thr Asn Tyr Ser Leu Lys Tyr Lys Leu Arg Trp Tyr<br>165                     170                   175 | | 585 |
| GGC CAG GAC AAC ACA TGT GAG GAG TAC CAC ACA GTG GGG CCC CAC TCC<br>Gly Gln Asp Asn Thr Cys Glu Glu Tyr His Thr Val Gly Pro His Ser<br>180                     185                   190 | | 633 |
| TGC CAC ATC CCC AAG GAC CTG GCT CTC TTT ACG CCC TAT GAG ATC TGG<br>Cys His Ile Pro Lys Asp Leu Ala Leu Phe Thr Pro Tyr Glu Ile Trp<br>195                   200                   205               210 | | 681 |
| GTG GAG GCC ACC AAC CGC CTG GGC TCT GCC CGC TCC GAT GTA CTC ACG<br>Val Glu Ala Thr Asn Arg Leu Gly Ser Ala Arg Ser Asp Val Leu Thr<br>               215                   220               225 | | 729 |
| CTG GAT ATC CTG GAT GTG GTG ACC ACG GAC CCC CCG CCC GAA GTG CAC<br>Leu Asp Ile Leu Asp Val Val Thr Thr Asp Pro Pro Pro Glu Val His<br>             230                   235                   240 | | 777 |
| GTG AGC CGC GTC GGG GGC CTG GAG GAC CAG CTG AGC GTG CGC TGG GTG<br>Val Ser Arg Val Gly Gly Leu Glu Asp Gln Leu Ser Val Arg Trp Val<br>        245                    250                   255 | | 825 |
| TCG CCA CCC GCC CTC AAG GAT TTC CTC TTT CAA GCC AAA TAC CAG ATC<br>Ser Pro Pro Ala Leu Lys Asp Phe Leu Phe Gln Ala Lys Tyr Gln Ile<br>260                   265                   270 | | 873 |
| CGC TAC CGA GTG GAG GAC AGT GTG GAC TGG AAG GTG GTG GAC GAT GTG<br>Arg Tyr Arg Val Glu Asp Ser Val Asp Trp Lys Val Val Asp Asp Val<br>275                     280                   285               290 | | 921 |
| AGC AAC CAG ACC TCC TGC CGC CTG GCC GGC CTG AAA CCC GGC ACC GTG<br>Ser Asn Gln Thr Ser Cys Arg Leu Ala Gly Leu Lys Pro Gly Thr Val<br>               295                   300               305 | | 969 |
| TAC TTC GTG CAA GTG CGC TGC AAC CCC TTT GGC ATC TAT GGC TCC AAG<br>Tyr Phe Val Gln Val Arg Cys Asn Pro Phe Gly Ile Tyr Gly Ser Lys<br>        310                    315               320 | | 1017 |
| AAA GCC GGG ATC TGG AGT GAG TGG AGC CAC CCC ACA GCC GCC TCC ACT<br>Lys Ala Gly Ile Trp Ser Glu Trp Ser His Pro Thr Ala Ala Ser Thr<br>325                     330                   335 | | 1065 |

```
CCC CGC AGT GAG CGC CCG GGC CCG GGC GGC GGG GCG TGC GAA CCG CGG    1113
Pro Arg Ser Glu Arg Pro Gly Pro Gly Gly Gly Ala Cys Glu Pro Arg
    340                 345                 350

GGC GGA GAG CCG AGC TCG GGG CCG GTG CGG CGC GAG CTC AAG CAG TTC    1161
Gly Gly Glu Pro Ser Ser Gly Pro Val Arg Arg Glu Leu Lys Gln Phe
355                 360                 365                 370

CTG GGC TGG CTC AAG AAG CAC GCG TAC TGC TCC AAC CTC AGC TTC CGC    1209
Leu Gly Trp Leu Lys Lys His Ala Tyr Cys Ser Asn Leu Ser Phe Arg
                375                 380                 385

CTC TAC GAC CAG TGG CGA GCC TGG ATG CAG AAG TCG CAC AAG ACC CGC    1257
Leu Tyr Asp Gln Trp Arg Ala Trp Met Gln Lys Ser His Lys Thr Arg
            390                 395                 400

AAC CAG GAC GAG GGG ATC CTG CCC TCG GGC AGA CGG GGC ACG GCG AGA    1305
Asn Gln Asp Glu Gly Ile Leu Pro Ser Gly Arg Arg Gly Thr Ala Arg
        405                 410                 415

GGT CCT GCC AGA TAAGCTGTAG GGGCTCAGGC CACCCTCCCT GCCACGTGGA GACGC   1362
Gly Pro Ala Arg
    420

AGAGGCCGAA CCCAAACTGG GGCCACCTCT GTACCCTCAC TTCAGGGCAC CTGAGCCACC   1422

CTCAGCAAGA GCTGGGGTGG CCCCTGAGCT CCAACGGCCA TAACAGCTCT GACTCCCACG   1482

TGAGGCCACC TTTGGGTGCA CCCCAGTGGG TGTGTGTGTG TGTGTGAGGG TTGGTTGAGT   1542

TGCCTAGAAC CCCTGCCAGG GCTGGGGGTG AGAAGGGGAG TCATTACTCC CCATTACCTA   1602

GGGCCCCTCC AAAAGAGTCC TTTTAAATAA ATGAGCTATT TAGGTGCAAA AAAAAAAAA    1662

AAAAAAAAT TGCCCTCGTG CCGAATTC                                      1690
```

(2) INFORMATION FOR SEQ ID NO:2:

(i) SEQUENCE CHARACTERISTICS:
        (A) LENGTH: 422 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:2:

```
Met Pro Ala Gly Arg Gly Pro Ala Ala Gln Ser Ala Arg Arg Pro
1               5                   10                  15

Pro Pro Leu Leu Pro Leu Leu Leu Leu Cys Val Leu Gly Ala Pro
                20                  25                  30

Arg Ala Gly Ser Gly Ala His Thr Ala Val Ile Ser Pro Gln Asp Pro
        35                  40                  45

Thr Leu Leu Ile Gly Ser Ser Leu Leu Ala Thr Cys Ser Val His Gly
    50                  55                  60

Asp Pro Pro Gly Ala Thr Ala Glu Gly Leu Tyr Trp Thr Leu Asn Gly
65                  70                  75                  80

Arg Arg Leu Pro Pro Glu Leu Ser Arg Val Leu Asn Ala Ser Thr Leu
                85                  90                  95

Ala Leu Ala Leu Ala Asn Leu Asn Gly Ser Arg Gln Arg Ser Gly Asp
                100                 105                 110

Asn Leu Val Cys His Ala Arg Asp Gly Ser Ile Leu Ala Gly Ser Cys
            115                 120                 125

Leu Tyr Val Gly Leu Pro Pro Glu Lys Pro Val Asn Ile Ser Cys Trp
        130                 135                 140
```

```
Ser Lys Asn Met Lys Asp Leu Thr Cys Arg Trp Thr Pro Gly Ala His
145                 150                 155                 160

Gly Glu Thr Phe Leu His Thr Asn Tyr Ser Leu Lys Tyr Lys Leu Arg
                165                 170                 175

Trp Tyr Gly Gln Asp Asn Thr Cys Glu Glu Tyr His Thr Val Gly Pro
            180                 185                 190

His Ser Cys His Ile Pro Lys Asp Leu Ala Leu Phe Thr Pro Tyr Glu
        195                 200                 205

Ile Trp Val Glu Ala Thr Asn Arg Leu Gly Ser Ala Arg Ser Asp Val
210                 215                 220

Leu Thr Leu Asp Ile Leu Asp Val Val Thr Thr Asp Pro Pro Pro Glu
225                 230                 235                 240

Val His Val Ser Arg Val Gly Gly Leu Glu Asp Gln Leu Ser Val Arg
                245                 250                 255

Trp Val Ser Pro Pro Ala Leu Lys Asp Phe Leu Phe Gln Ala Lys Tyr
            260                 265                 270

Gln Ile Arg Tyr Arg Val Glu Asp Ser Val Asp Trp Lys Val Val Asp
        275                 280                 285

Asp Val Ser Asn Gln Thr Ser Cys Arg Leu Ala Gly Leu Lys Pro Gly
290                 295                 300

Thr Val Tyr Phe Val Gln Val Arg Cys Asn Pro Phe Gly Ile Tyr Gly
305                 310                 315                 320

Ser Lys Lys Ala Gly Ile Trp Ser Glu Trp Ser His Pro Thr Ala Ala
                325                 330                 335

Ser Thr Pro Arg Ser Glu Arg Pro Gly Pro Gly Gly Ala Cys Glu
            340                 345                 350

Pro Arg Gly Gly Glu Pro Ser Ser Gly Pro Val Arg Arg Glu Leu Lys
        355                 360                 365

Gln Phe Leu Gly Trp Leu Lys Lys His Ala Tyr Cys Ser Asn Leu Ser
370                 375                 380

Phe Arg Leu Tyr Asp Gln Trp Arg Ala Trp Met Gln Lys Ser His Lys
385                 390                 395                 400

Thr Arg Asn Gln Asp Glu Gly Ile Leu Pro Ser Gly Arg Arg Gly Thr
                405                 410                 415

Ala Arg Gly Pro Ala Arg
            420
```

2) INFORMATION FOR SEQ ID NO:3:

(i) SEQUENCE CHARACTERISTICS:
        (A) LENGTH: 1813 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 88...1362
        (D) OTHER INFORMATION:

(xi) SEQUENCE DESCRIPTION: SEQ ID NO:3:

```
AATTCGGCAC GAGGGGCCTG CGTCCCGCGC CGTGCGCCAC CGCCGCCGAG CCGCAGCCCG      60

CCGCGCGCCC CCGGCAGCGC CGGCCCC ATG CCC GCC GGC CGC CGG GGC CCC GCC     114
                            Met Pro Ala Gly Arg Arg Gly Pro Ala
                              1               5

GCC CAA TCC GCG CGG CGG CCG CCG CCG TTG CTG CCC CTG CTG CTG CTC       162
```

```
Ala Gln Ser Ala Arg Arg Pro Pro Leu Leu Pro Leu Leu Leu Leu
 10              15              20              25

TGC GTC CTC GGG GCG CCG CGA GCC GGA TCA GGA GCC CAC ACA GCT GTG       210
Cys Val Leu Gly Ala Pro Arg Ala Gly Ser Gly Ala His Thr Ala Val
             30              35              40

ATC AGT CCC CAG GAT CCC ACG CTT CTC ATC GGC TCC TCC CTG CTG GCC       258
Ile Ser Pro Gln Asp Pro Thr Leu Leu Ile Gly Ser Ser Leu Leu Ala
             45              50              55

ACC TGC TCA GTG CAC GGA GAC CCA CCA GGA GCC ACC GCC GAG GGC CTC       306
Thr Cys Ser Val His Gly Asp Pro Pro Gly Ala Thr Ala Glu Gly Leu
         60              65              70

TAC TGG ACC CTC AAT GGG CGC CGC CTG CCC CCT GAG CTC TCC CGT GTA       354
Tyr Trp Thr Leu Asn Gly Arg Arg Leu Pro Pro Glu Leu Ser Arg Val
     75              80              85

CTC AAC GCC TCC ACC TTG GCT CTG GCC CTG GCC AAC CTC AAT GGG TCC       402
Leu Asn Ala Ser Thr Leu Ala Leu Ala Leu Ala Asn Leu Asn Gly Ser
 90              95             100             105

AGG CAG CGG TCG GGG GAC AAC CTC GTG TGC CAC GCC CGT GAC GGC AGC       450
Arg Gln Arg Ser Gly Asp Asn Leu Val Cys His Ala Arg Asp Gly Ser
                110             115             120

ATC CTG GCT GGC TCC TGC CTC TAT GTT GGC CTG CCC CCA GAG AAA CCC       498
Ile Leu Ala Gly Ser Cys Leu Tyr Val Gly Leu Pro Pro Glu Lys Pro
            125             130             135

GTC AAC ATC AGC TGC TGG TCC AAG AAC ATG AAG GAC TTG ACC TGC CGC       546
Val Asn Ile Ser Cys Trp Ser Lys Asn Met Lys Asp Leu Thr Cys Arg
            140             145             150

TGG ACG CCA GGG GCC CAC GGG GAG ACC TTC CTC CAC ACC AAC TAC TCC       594
Trp Thr Pro Gly Ala His Gly Glu Thr Phe Leu His Thr Asn Tyr Ser
        155             160             165

CTC AAG TAC AAG CTT AGG TGG TAT GGC CAG GAC AAC ACA TGT GAG GAG       642
Leu Lys Tyr Lys Leu Arg Trp Tyr Gly Gln Asp Asn Thr Cys Glu Glu
170             175             180             185

TAC CAC ACA GTG GGG CCC CAC TCC TGC CAC ATC CCC AAG GAC CTG GCT       690
Tyr His Thr Val Gly Pro His Ser Cys His Ile Pro Lys Asp Leu Ala
                190             195             200

CTC TTT ACG CCC TAT GAG ATC TGG GTG GAG GCC ACC AAC CGC CTG GGC       738
Leu Phe Thr Pro Tyr Glu Ile Trp Val Glu Ala Thr Asn Arg Leu Gly
            205             210             215

TCT GCC CGC TCC GAT GTA CTC ACG CTG GAT ATC CTG GAT GTG GTG ACC       786
Ser Ala Arg Ser Asp Val Leu Thr Leu Asp Ile Leu Asp Val Val Thr
            220             225             230

ACG GAC CCC CCG CCC GAC GTG CAC GTG AGC CGC GTC GGG GGC CTG GAG       834
Thr Asp Pro Pro Pro Asp Val His Val Ser Arg Val Gly Gly Leu Glu
        235             240             245

GAC CAG CTG AGC GTG CGC TGG GTG TCG CCA CCC GCC CTC AAG GAT TTC       882
Asp Gln Leu Ser Val Arg Trp Val Ser Pro Pro Ala Leu Lys Asp Phe
250             255             260             265

CTC TTT CAA GCC AAA TAC CAG ATC CGC TAC CGA GTG GAG GAC AGT GTG       930
Leu Phe Gln Ala Lys Tyr Gln Ile Arg Tyr Arg Val Glu Asp Ser Val
            270             275             280

GAC TGG AAG GTG GTG GAC GAT GTG AGC AAC CAG ACC TCC TGC CGC CTG       978
Asp Trp Lys Val Val Asp Asp Val Ser Asn Gln Thr Ser Cys Arg Leu
            285             290             295

GCC GGC CTG AAA CCC GGC ACC GTG TAC TTC GTG CAA GTG CGC TGC AAC      1026
Ala Gly Leu Lys Pro Gly Thr Val Tyr Phe Val Gln Val Arg Cys Asn
            300             305             310

CCC TTT GGC ATC TAT GGC TCC AAG AAA GCC GGG ATC TGG AGT GAG TGG      1074
Pro Phe Gly Ile Tyr Gly Ser Lys Lys Ala Gly Ile Trp Ser Glu Trp
        315             320             325
```

-continued

```
AGC CAC CCC ACA GCC GCC TCC ACT CCC CGC AGT GAG CGC CCG GGC CCG    1122
Ser His Pro Thr Ala Ala Ser Thr Pro Arg Ser Glu Arg Pro Gly Pro
330                 335                 340                 345

GGC GGC GGG GCG TGC GAA CCG CGG GGC GGA GAG CCG AGC TCG GGG CCG    1170
Gly Gly Gly Ala Cys Glu Pro Arg Gly Gly Glu Pro Ser Ser Gly Pro
            350                 355                 360

GTG CGG CGC GAG CTC AAG CAG TTC CTG GGC TGG CTC AAG AAG CAC GCG    1218
Val Arg Arg Glu Leu Lys Gln Phe Leu Gly Trp Leu Lys Lys His Ala
                365                 370                 375

TAC TGC TCC AAC CTC AGC TTC CGC CTC TAC GAC CAG TGG CGA GCC TGG    1266
Tyr Cys Ser Asn Leu Ser Phe Arg Leu Tyr Asp Gln Trp Arg Ala Trp
            380                 385                 390

ATG CAG AAG TCG CAC AAG ACC CGC AAC CAG CAC AGG ACG AGG GGA TCC    1314
Met Gln Lys Ser His Lys Thr Arg Asn Gln His Arg Thr Arg Gly Ser
395                 400                 405

TGC CCT CGG GCA GAC GGG GCA CGG CGA GAG GTC CTG CCA GAT AAG CTG T 1363
Cys Pro Arg Ala Asp Gly Ala Arg Arg Glu Val Leu Pro Asp Lys Leu
410                 415                 420                 425

AGGGGCTCAG GCCACCCTCC CTGCCACGTG GAGACGCAGA GGCCGAACCC AAACTGGGGC  1423

CACCTCTGTA CCCTCACTTC AGGGCACCTG AGCCACCCTC AGCAGGAGCT GGGGTGGCCC  1483

CTGAGCTCCA ACGGCCATAA CAGCTCTGAC TCCCACGTGA GGCCACCTTT GGGTGCACCC  1543

CAGTGGGTGT GTGTGTGTGT GTGAGGGTTG GTTGAGTTGC CTAGAACCCC TGCCAGGGCT  1603

GGGGGTGAGA AGGGGAGTCA TTACTCCCCA TTACCTAGGG CCCCTCCAAA AGAGTCCTTT  1663

TAAATAAATG AGCTATTTAG GTGCAAAAAA AAAAAAAAAA AAAAAAAAAA AAAAAAAAAA  1723

AAAAAAAAAA AAAAAAAAAA AAAAAAAAAA AAAAAAAAAA AAAAAAAAAA AAAAAAAAAA  1783

AAAAAAAAAA AAAAAAAAT TTCCCGGGGA                                    1813
```

(2) INFORMATION FOR SEQ ID NO:4:

(i) SEQUENCE CHARACTERISTICS:
        (A) LENGTH: 425 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:4:

```
Met Pro Ala Gly Arg Arg Gly Pro Ala Ala Gln Ser Ala Arg Pro
1               5                   10                  15

Pro Pro Leu Leu Pro Leu Leu Leu Cys Val Leu Gly Ala Pro Arg
                20                  25                  30

Ala Gly Ser Gly Ala His Thr Ala Val Ile Ser Pro Gln Asp Pro Thr
            35                  40                  45

Leu Leu Ile Gly Ser Ser Leu Leu Ala Thr Cys Ser Val His Gly Asp
        50                  55                  60

Pro Pro Gly Ala Thr Ala Glu Gly Leu Tyr Trp Thr Leu Asn Gly Arg
65                  70                  75                  80

Arg Leu Pro Pro Glu Leu Ser Arg Val Leu Asn Ala Ser Thr Leu Ala
                85                  90                  95

Leu Ala Leu Ala Asn Leu Asn Gly Ser Arg Gln Arg Ser Gly Asp Asn
                100                 105                 110

Leu Val Cys His Ala Arg Asp Gly Ser Ile Leu Ala Gly Ser Cys Leu
            115                 120                 125
```

```
Tyr Val Gly Leu Pro Pro Glu Lys Pro Val Asn Ile Ser Cys Trp Ser
    130                 135                 140

Lys Asn Met Lys Asp Leu Thr Cys Arg Trp Thr Pro Gly Ala His Gly
145                 150                 155                 160

Glu Thr Phe Leu His Thr Asn Tyr Ser Leu Lys Tyr Lys Leu Arg Trp
                165                 170                 175

Tyr Gly Gln Asp Asn Thr Cys Glu Glu Tyr His Thr Val Gly Pro His
            180                 185                 190

Ser Cys His Ile Pro Lys Asp Leu Ala Leu Phe Thr Pro Tyr Glu Ile
            195                 200                 205

Trp Val Glu Ala Thr Asn Arg Leu Gly Ser Ala Arg Ser Asp Val Leu
    210                 215                 220

Thr Leu Asp Ile Leu Asp Val Val Thr Thr Asp Pro Pro Asp Val
225                 230                 235                 240

His Val Ser Arg Val Gly Gly Leu Glu Asp Gln Leu Ser Val Arg Trp
                245                 250                 255

Val Ser Pro Pro Ala Leu Lys Asp Phe Leu Phe Gln Ala Lys Tyr Gln
            260                 265                 270

Ile Arg Tyr Arg Val Glu Asp Ser Val Asp Trp Lys Val Val Asp Asp
            275                 280                 285

Val Ser Asn Gln Thr Ser Cys Arg Leu Ala Gly Leu Lys Pro Gly Thr
    290                 295                 300

Val Tyr Phe Val Gln Val Arg Cys Asn Pro Phe Gly Ile Tyr Gly Ser
305                 310                 315                 320

Lys Lys Ala Gly Ile Trp Ser Glu Trp Ser His Pro Thr Ala Ala Ser
                325                 330                 335

Thr Pro Arg Ser Glu Arg Pro Gly Pro Gly Gly Ala Cys Glu Pro
            340                 345                 350

Arg Gly Gly Glu Pro Ser Ser Gly Pro Val Arg Arg Glu Leu Lys Gln
    355                 360                 365

Phe Leu Gly Trp Leu Lys Lys His Ala Tyr Cys Ser Asn Leu Ser Phe
370                 375                 380

Arg Leu Tyr Asp Gln Trp Arg Ala Trp Met Gln Lys Ser His Lys Thr
385                 390                 395                 400

Arg Asn Gln His Arg Thr Arg Gly Ser Cys Pro Arg Ala Asp Gly Ala
            405                 410                 415

Arg Arg Glu Val Leu Pro Asp Lys Leu
            420                 425

(2) INFORMATION FOR SEQ ID NO:5:

(i) SEQUENCE CHARACTERISTICS:
        (A) LENGTH: 1724 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 159...1433
        (D) OTHER INFORMATION:

(xi) SEQUENCE DESCRIPTION: SEQ ID NO:5:

GAATTCGGCA CGAGGAATTT CGGCTGCTCA GACTTGCTCC GGCCTTCGCT GTCCGCGCCC        60

AGTGACGTGC GTGCGGACCC AAACCCCAAT CTGCACCCCG CAGAGTCGCC CCCGCCCCAT      120
```

```
                                                                    -continued ACCGGCGTTG CAGTCACCGC CCGTTGCGCG CCACCCCC ATG CCC GCC GGT GGC CCG        176
                                             Met Pro Ala Gly Gly Pro
                                             1               5

GGC CCC GCC GCC CAA TCC GCG CGG CGG CCG CCG CGG CGG CTC TCC TCG         224
Gly Pro Ala Ala Gln Ser Ala Arg Arg Pro Pro Arg Arg Leu Ser Ser
            10                  15                  20

CTG TGG TCG CCT CTG TTG CTC TGT GTT CTC GGG GTG CCT CAG GGC GGA         272
Leu Trp Ser Pro Leu Leu Leu Cys Val Leu Gly Val Pro Gln Gly Gly
        25                  30                  35

TCG GGA GCC CAC ACA GCT GTG ATC AGT CCC CAG GAC CCC ACT CTT CTC         320
Ser Gly Ala His Thr Ala Val Ile Ser Pro Gln Asp Pro Thr Leu Leu
    40                  45                  50

ATC GGA TCC TCC CTT CAT GCT ACG TGC TCT ATA CAT GGA GAC ACA CCG         368
Ile Gly Ser Ser Leu His Ala Thr Cys Ser Ile His Gly Asp Thr Pro
55                  60                  65                  70

GGG GCC ACT GCT GAG GGC CTC TAC TGG ACC CTC AAC GGC CGC CGC CTG         416
Gly Ala Thr Ala Glu Gly Leu Tyr Trp Thr Leu Asn Gly Arg Arg Leu
                75                  80                  85

CCC TCA GAG CTG TCC CGT CTC CTC AAC ACC TCC ACC CTG GCC TTG GCC         464
Pro Ser Glu Leu Ser Arg Leu Leu Asn Thr Ser Thr Leu Ala Leu Ala
            90                  95                 100

CTG GCT AAC CTT AAT GGG TCC AGG CAG CAG TCA GGG GAC AAT CTG GTG         512
Leu Ala Asn Leu Asn Gly Ser Arg Gln Gln Ser Gly Asp Asn Leu Val
        105                 110                 115

TGT CAC GCC CGA GAT GGC AGC ATT CTG GCT GGT TCC TGC CTC TAT GTT         560
Cys His Ala Arg Asp Gly Ser Ile Leu Ala Gly Ser Cys Leu Tyr Val
    120                 125                 130

GGT CTG CCC CCG GAG AAG CCC TTT AAC ATC AGC TGC TGG TCC CGG AAC         608
Gly Leu Pro Pro Glu Lys Pro Phe Asn Ile Ser Cys Trp Ser Arg Asn
135                 140                 145                 150

ATG AAG GAC CTG ACA TGC CGT TGG ACA CCG GGT GCA CAT GGG GAG ACA         656
Met Lys Asp Leu Thr Cys Arg Trp Thr Pro Gly Ala His Gly Glu Thr
                155                 160                 165

TTC CTA CAC ACC AAC TAC TCC CTC AAG TAC AAG CTG AGG TGG TAT GGT         704
Phe Leu His Thr Asn Tyr Ser Leu Lys Tyr Lys Leu Arg Trp Tyr Gly
            170                 175                 180

CAG GAC AAC ACA TGT GAG GAA TAT CAC ACT GTG GGC CCT CAC TCG TGC         752
Gln Asp Asn Thr Cys Glu Glu Tyr His Thr Val Gly Pro His Ser Cys
        185                 190                 195

CAT ATC CCC AAA GAC CTG GCC CTC TTC ACG CCC TAT GAG ATC TGG GTG         800
His Ile Pro Lys Asp Leu Ala Leu Phe Thr Pro Tyr Glu Ile Trp Val
    200                 205                 210

GAA GCC ACC AAT CGC CTG GGT TCA GCG AGA TCT GAC GTG CTC ACA CTG         848
Glu Ala Thr Asn Arg Leu Gly Ser Ala Arg Ser Asp Val Leu Thr Leu
215                 220                 225                 230

GAT GTC CTG GAC GTG GTG ACC ACG GAC CCT CCA CCC GAC GTG CAC GTG         896
Asp Val Leu Asp Val Val Thr Thr Asp Pro Pro Pro Asp Val His Val
                235                 240                 245

AGC CGC GTT GGG GGC CTG GAG GAC CAG CTG AGT GTG CGC TGG GTC TCA         944
Ser Arg Val Gly Gly Leu Glu Asp Gln Leu Ser Val Arg Trp Val Ser
            250                 255                 260

CCA CCA GCT CTC AAG GAT TTC CTC TTC CAA GCC AAA TAC CAG ATT CGC         992
Pro Pro Ala Leu Lys Asp Phe Leu Phe Gln Ala Lys Tyr Gln Ile Arg
        265                 270                 275

TAC CGC GTG GAG GAC AGC GTG GAC TGG AAG GTG GTG GAT GAC GTC AGC        1040
Tyr Arg Val Glu Asp Ser Val Asp Trp Lys Val Val Asp Asp Val Ser
    280                 285                 290

AAC CAG ACC TCC TGC CGT CTC GCG GGC TTG AAG CCC GGC ACC GTT TAC        1088
Asn Gln Thr Ser Cys Arg Leu Ala Gly Leu Lys Pro Gly Thr Val Tyr
295                 300                 305                 310
```

```
TTC GTC CAA GTT CGT TGT AAC CCA TTC GGG ATC TAT GGG TCG AAA AAG         1136
Phe Val Gln Val Arg Cys Asn Pro Phe Gly Ile Tyr Gly Ser Lys Lys
                315                 320                 325

GCG GGA ATC TGG AGC GAG TGG AGC CAC CCC ACC GCT GCC TCC ACC CCT         1184
Ala Gly Ile Trp Ser Glu Trp Ser His Pro Thr Ala Ala Ser Thr Pro
            330                 335                 340

CGA AGT GAG CGC CCG GGC CCG GGC GGC GGG GTG TGC GAG CCG CGG GGC         1232
Arg Ser Glu Arg Pro Gly Pro Gly Gly Gly Val Cys Glu Pro Arg Gly
        345                 350                 355

GGC GAG CCT AGC TCG GGC CCG GTG CGG CGC GAG CTC AAG CAG TTC CTC         1280
Gly Glu Pro Ser Ser Gly Pro Val Arg Arg Glu Leu Lys Gln Phe Leu
    360                 365                 370

GGC TGG CTC AAG AAG CAC GCG TAC TGC TCG AAC CTT AGC TTC CGC CTG         1328
Gly Trp Leu Lys Lys His Ala Tyr Cys Ser Asn Leu Ser Phe Arg Leu
375                 380                 385                 390

TAC GAC CAG TGG CGT GCT TGG ATG CAG AAG TCA CAC AAG ACC CGA AAC         1376
Tyr Asp Gln Trp Arg Ala Trp Met Gln Lys Ser His Lys Thr Arg Asn
                395                 400                 405

CAG GAC GAG GGG ATC CTG CCC TCG GGC AGA CGG GGT GCG GCG AGA GGT         1424
Gln Asp Glu Gly Ile Leu Pro Ser Gly Arg Arg Gly Ala Ala Arg Gly
            410                 415                 420

CCT GCC GGC TAAACTCTGA GGATAGGCCA TCCTCCTGCT GGATGCAGAC CTGGAGGCT      1482
Pro Ala Gly
        425

CACCTGAACT GGAGACCATC TGTACTGTCA CTTTGGGGCA ATGAAGAAAC AAACCAGGGG      1542

CTGGGGCACA ATGAGCTCCC ACAACCACAG CTTTGCCAC ATGATGGTCA ACTTTGGATG       1602

TACCCCAATA TGGGTAGGGT TGGAGTAATG ACAAGGGTTA TGCAGGACCC TCCAAGAGTC     1662

TCTTTGAATA AATAAGAAAA GAGTTGTTCA GGAAAAAAAA AAAAAAAAAA AATAGCGGCC    1722

GC                                                                      1724

(2) INFORMATION FOR SEQ ID NO:6:

(i) SEQUENCE CHARACTERISTICS:
          (A) LENGTH: 425 amino acids
          (B) TYPE: amino acid
          (C) STRANDEDNESS: single
          (D) TOPOLOGY: linear (ii) MOLECULE TYPE: protein (v) FRAGMENT TYPE: internal (xi) SEQUENCE DESCRIPTION: SEQ ID NO:6:

Met Pro Ala Gly Gly Pro Gly Ala Ala Gln Ser Ala Arg Arg Pro
1               5                   10                  15

Pro Arg Arg Leu Ser Ser Leu Trp Ser Pro Leu Leu Leu Cys Val Leu
                20                  25                  30

Gly Val Pro Gln Gly Gly Ser Gly Ala His Thr Ala Val Ile Ser Pro
            35                  40                  45

Gln Asp Pro Thr Leu Leu Ile Gly Ser Ser Leu His Ala Thr Cys Ser
        50                  55                  60

Ile His Gly Asp Thr Pro Gly Ala Thr Ala Glu Gly Leu Tyr Trp Thr
65                  70                  75                  80

Leu Asn Gly Arg Arg Leu Pro Ser Glu Leu Ser Arg Leu Leu Asn Thr
                85                  90                  95

Ser Thr Leu Ala Leu Ala Leu Ala Asn Leu Asn Gly Ser Arg Gln Gln
            100                 105                 110
```

```
Ser Gly Asp Asn Leu Val Cys His Ala Arg Asp Gly Ser Ile Leu Ala
        115                 120                 125

Gly Ser Cys Leu Tyr Val Gly Leu Pro Pro Glu Lys Pro Phe Asn Ile
    130                 135                 140

Ser Cys Trp Ser Arg Asn Met Lys Asp Leu Thr Cys Arg Trp Thr Pro
145                 150                 155                 160

Gly Ala His Gly Glu Thr Phe Leu His Thr Asn Tyr Ser Leu Lys Tyr
                165                 170                 175

Lys Leu Arg Trp Tyr Gly Gln Asp Asn Thr Cys Glu Glu Tyr His Thr
            180                 185                 190

Val Gly Pro His Ser Cys His Ile Pro Lys Asp Leu Ala Leu Phe Thr
            195                 200                 205

Pro Tyr Glu Ile Trp Val Glu Ala Thr Asn Arg Leu Gly Ser Ala Arg
210                 215                 220

Ser Asp Val Leu Thr Leu Asp Val Leu Asp Val Val Thr Thr Asp Pro
225                 230                 235                 240

Pro Pro Asp Val His Val Ser Arg Val Gly Gly Leu Glu Asp Gln Leu
                245                 250                 255

Ser Val Arg Trp Val Ser Pro Pro Ala Leu Lys Asp Phe Leu Phe Gln
            260                 265                 270

Ala Lys Tyr Gln Ile Arg Tyr Arg Val Glu Asp Ser Val Asp Trp Lys
            275                 280                 285

Val Val Asp Asp Val Ser Asn Gln Thr Ser Cys Arg Leu Ala Gly Leu
290                 295                 300

Lys Pro Gly Thr Val Tyr Phe Val Gln Val Arg Cys Asn Pro Phe Gly
305                 310                 315                 320

Ile Tyr Gly Ser Lys Lys Ala Gly Ile Trp Ser Glu Trp Ser His Pro
                325                 330                 335

Thr Ala Ala Ser Thr Pro Arg Ser Glu Arg Pro Gly Pro Gly Gly Gly
            340                 345                 350

Val Cys Glu Pro Arg Gly Gly Glu Pro Ser Ser Gly Pro Val Arg Arg
            355                 360                 365

Glu Leu Lys Gln Phe Leu Gly Trp Leu Lys Lys His Ala Tyr Cys Ser
370                 375                 380

Asn Leu Ser Phe Arg Leu Tyr Asp Gln Trp Arg Ala Trp Met Gln Lys
385                 390                 395                 400

Ser His Lys Thr Arg Asn Gln Asp Glu Gly Ile Leu Pro Ser Gly Arg
                405                 410                 415

Arg Gly Ala Ala Arg Gly Pro Ala Gly
            420                 425

(2) INFORMATION FOR SEQ ID NO:7:

(i) SEQUENCE CHARACTERISTICS:
        (A) LENGTH: 259 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:7:

AGGATTTCCT CTTTCAAGCC AAATACCAGA TCCGCTANCG AGTGGAGGAN AGTGTGGANT     60

GGAAGGTGGT GGANGATGTG AGCAACCAGA CCTTCTGCCG CTGGNCGGCC TGAAACCCGG    120

CANCGTGTAC TTCGTGCAAG TGCGCTGCAA NCCCTTTGGC ATCTATGGCT NCAAGAAAGC    180
```

```
CGGGATCTNG AGTGAGTGGA GCCANCCCAC AGCCGGCTTC ANTTCCCGCA GTGAGCGNCN    240

GGGCCCGGGN GGNGGGAAG                                                 259
```

(2) INFORMATION FOR SEQ ID NO:8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:8:

```
CGCGAGCTCA AGCAGTTCCT G                                              21
```

(2) INFORMATION FOR SEQ ID NO:9:

(i) SEQUENCE CHARACTERISTICS:
        (A) LENGTH: 210 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:9:

```
GNACACGCCG NTATAGCTNG CCCCTGCTGC TGCTGCTCTG CGTCCTCGGG GCNCGCGAGC     60

GGATTCAGGA GCCCACACAG CTGTGATCAG TCCCCAGGAT CCCACGCTTC TCATCGGCTC    120

CTCCCTGCTG GCCACCTGCT CAGTGCACGG AGACCCACCA GGAGCCACCG CCGAGGGCCT    180

CTACTGGACC CTCAACGGGC GCCGCTGCCC                                     210
```

(2) INFORMATION FOR SEQ ID NO:10:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:10:

```
CCACCTAAGC TTGTACTTGA GG                                             22
```

(2) INFORMATION FOR SEQ ID NO:11:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:11:

```
AGCCCACACA GCTGTGATCA G                                              21
```

(2) INFORMATION FOR SEQ ID NO:12:

(i) SEQUENCE CHARACTERISTICS:
        (A) LENGTH: 44 base pairs
        (B) TYPE: nucleic acid
        (C) STRANDEDNESS: single
        (D) TOPOLOGY: linear -continued (ii) MOLECULE TYPE: Other (xi) SEQUENCE DESCRIPTION: SEQ ID NO:12:

GACAGAGCAC AGAATTCACT AGTGAGCTCT TTTTTTTTTT TTTT                    44

(2) INFORMATION FOR SEQ ID NO:13:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:13:

TATGGCCAGG ACAACACA                                                18

(2) INFORMATION FOR SEQ ID NO:14:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:14:

ATAGGGCGTA AAGAGAGC                                                18

(2) INFORMATION FOR SEQ ID NO:15:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:15:

TCACATCGTC CACCACCTTC CAGTCCA                                      27

(2) INFORMATION FOR SEQ ID NO:16:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:16:

GAGCACAGAA TTCACTACTC GAGGCGGCCG CTTTTTTTTT TTTTTTTTT              49

(2) INFORMATION FOR SEQ ID NO:17:

(i) SEQUENCE CHARACTERISTICS:
        (A) LENGTH: 388 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:17:

```
Gly Ser Gly Ala His Thr Ala Val Ile Ser Pro Gln Asp Pro Thr Leu
1               5                   10                  15

Leu Ile Gly Ser Ser Leu Leu Ala Thr Cys Ser Val His Gly Asp Pro
            20                  25                  30

Pro Gly Ala Thr Ala Glu Gly Leu Tyr Trp Thr Leu Xaa Gly Arg Arg
            35                  40                  45

Leu Pro Pro Glu Leu Ser Arg Val Leu Asn Ala Ser Thr Leu Ala Leu
    50                  55                  60

Ala Leu Ala Asn Leu Asn Gly Ser Arg Gln Arg Ser Gly Asp Asn Leu
65                  70                  75                  80

Val Cys His Ala Arg Asp Gly Ser Ile Leu Ala Gly Ser Cys Leu Tyr
                85                  90                  95

Val Gly Leu Pro Pro Glu Lys Pro Val Asn Ile Ser Cys Trp Ser Lys
            100                 105                 110

Asn Met Lys Asp Leu Thr Cys Arg Trp Thr Pro Gly Ala His Gly Glu
            115                 120                 125

Thr Phe Leu His Thr Asn Tyr Ser Leu Lys Tyr Lys Leu Arg Trp Tyr
            130                 135                 140

Gly Gln Asp Asn Thr Cys Glu Glu Tyr His Thr Val Gly Pro His Ser
145                 150                 155                 160

Cys His Ile Pro Lys Asp Leu Ala Leu Phe Thr Pro Tyr Glu Ile Trp
                165                 170                 175

Val Glu Ala Thr Asn Arg Leu Gly Ser Ala Arg Ser Asp Val Leu Thr
            180                 185                 190

Leu Asp Ile Leu Asp Val Val Thr Thr Asp Pro Pro Glu Val His
            195                 200                 205

Val Ser Arg Val Gly Gly Leu Glu Asp Gln Leu Ser Val Arg Trp Val
    210                 215                 220

Ser Pro Pro Ala Leu Lys Asp Phe Leu Phe Gln Ala Lys Tyr Gln Ile
225                 230                 235                 240

Arg Tyr Arg Val Glu Asp Ser Val Asp Trp Lys Val Val Asp Asp Val
            245                 250                 255

Ser Asn Gln Thr Ser Cys Arg Leu Ala Gly Leu Lys Pro Gly Thr Val
            260                 265                 270

Tyr Phe Val Gln Val Arg Cys Asn Pro Phe Gly Ile Tyr Gly Ser Lys
    275                 280                 285

Lys Ala Gly Ile Trp Ser Glu Trp Ser His Pro Thr Ala Ala Ser Thr
290                 295                 300

Pro Arg Ser Glu Arg Pro Gly Pro Gly Gly Ala Cys Glu Pro Arg
305                 310                 315                 320

Gly Gly Glu Pro Ser Ser Gly Pro Val Arg Arg Glu Leu Lys Gln Phe
                325                 330                 335

Leu Gly Trp Leu Lys Lys His Ala Tyr Cys Ser Asn Leu Ser Phe Arg
            340                 345                 350

Leu Tyr Asp Gln Trp Arg Ala Trp Met Gln Lys Ser His Lys Thr Arg
            355                 360                 365

Asn Gln Asp Glu Gly Ile Leu Pro Ser Gly Arg Arg Gly Thr Ala Arg
    370                 375                 380

Gly Pro Ala Arg
385
```

(2) INFORMATION FOR SEQ ID NO:18:

(i) SEQUENCE CHARACTERISTICS:

(A) LENGTH: 392 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:18:

```
Gly Ser Gly Ala His Thr Ala Val Ile Ser Pro Gln Asp Pro Thr Leu
  1               5                  10                  15

Leu Ile Gly Ser Ser Leu Leu Ala Thr Cys Ser Val His Gly Asp Pro
             20                  25                  30

Pro Gly Ala Thr Ala Glu Gly Leu Tyr Trp Thr Leu Asn Gly Arg Arg
         35                  40                  45

Leu Pro Pro Glu Leu Ser Arg Val Leu Asn Ala Ser Thr Leu Ala Leu
 50                  55                  60

Ala Leu Ala Asn Leu Asn Gly Ser Arg Gln Arg Ser Gly Asp Asn Leu
 65                  70                  75                  80

Val Cys His Ala Arg Asp Gly Ser Ile Leu Ala Gly Ser Cys Leu Tyr
                 85                  90                  95

Val Gly Leu Pro Pro Glu Lys Pro Val Asn Ile Ser Cys Trp Ser Lys
                100                 105                 110

Asn Met Lys Asp Leu Thr Cys Arg Trp Thr Pro Gly Ala His Gly Glu
            115                 120                 125

Thr Phe Leu His Thr Asn Tyr Ser Leu Lys Tyr Lys Leu Arg Trp Tyr
        130                 135                 140

Gly Gln Asp Asn Thr Cys Glu Glu Tyr His Thr Val Gly Pro His Ser
145                 150                 155                 160

Cys His Ile Pro Lys Asp Leu Ala Leu Phe Thr Pro Tyr Glu Ile Trp
                165                 170                 175

Val Glu Ala Thr Asn Arg Leu Gly Ser Ala Arg Ser Asp Val Leu Thr
                180                 185                 190

Leu Asp Ile Leu Asp Val Val Thr Thr Asp Pro Pro Asp Val His
            195                 200                 205

Val Ser Arg Val Gly Gly Leu Glu Asp Gln Leu Ser Val Arg Trp Val
        210                 215                 220

Ser Pro Pro Ala Leu Lys Asp Phe Leu Phe Gln Ala Lys Tyr Gln Ile
225                 230                 235                 240

Arg Tyr Arg Val Glu Asp Ser Val Asp Trp Lys Val Val Asp Asp Val
                245                 250                 255

Ser Asn Gln Thr Ser Cys Arg Leu Ala Gly Leu Lys Pro Gly Thr Val
            260                 265                 270

Tyr Phe Val Gln Val Arg Cys Asn Pro Phe Gly Ile Tyr Gly Ser Lys
        275                 280                 285

Lys Ala Gly Ile Trp Ser Glu Trp Ser His Pro Thr Ala Ala Ser Thr
290                 295                 300

Pro Arg Ser Glu Arg Pro Gly Pro Gly Gly Ala Cys Glu Pro Arg
305                 310                 315                 320

Gly Gly Glu Pro Ser Ser Gly Pro Val Arg Arg Glu Leu Lys Gln Phe
                325                 330                 335

Leu Gly Trp Leu Lys Lys His Ala Tyr Cys Ser Asn Leu Ser Phe Arg
            340                 345                 350

Leu Tyr Asp Gln Trp Arg Ala Trp Met Gln Lys Ser His Lys Thr Arg
        355                 360                 365

Asn Gln His Arg Thr Arg Gly Ser Cys Pro Arg Ala Asp Gly Ala Arg
```

```
                  370                 375                 380
Arg Glu Val Leu Pro Asp Lys Leu
385                 390
```

(2) INFORMATION FOR SEQ ID NO:19:

(i) SEQUENCE CHARACTERISTICS:
        (A) LENGTH: 385 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:19:

```
Ala His Thr Ala Val Ile Ser Pro Gln Asp Pro Thr Leu Leu Ile Gly
 1               5                  10                  15
Ser Ser Leu His Ala Thr Cys Ser Ile His Gly Asp Thr Pro Gly Ala
                20                  25                  30
Thr Ala Glu Gly Leu Tyr Trp Thr Leu Asn Gly Arg Arg Leu Pro Ser
            35                  40                  45
Glu Leu Ser Arg Leu Leu Asn Thr Ser Thr Leu Ala Leu Ala Leu Ala
    50                  55                  60
Asn Leu Asn Gly Ser Arg Gln Gln Ser Gly Asp Asn Leu Val Cys His
65                  70                  75                  80
Ala Arg Asp Gly Ser Ile Leu Ala Gly Ser Cys Leu Tyr Val Gly Leu
                85                  90                  95
Pro Pro Glu Lys Pro Phe Asn Ile Ser Cys Trp Ser Arg Asn Met Lys
            100                 105                 110
Asp Leu Thr Cys Arg Trp Thr Pro Gly Ala His Gly Glu Thr Phe Leu
    115                 120                 125
His Thr Asn Tyr Ser Leu Lys Tyr Lys Leu Arg Trp Tyr Gly Gln Asp
130                 135                 140
Asn Thr Cys Glu Glu Tyr His Thr Val Gly Pro His Ser Cys His Ile
145                 150                 155                 160
Pro Lys Asp Leu Ala Leu Phe Thr Pro Tyr Glu Ile Trp Val Glu Ala
                165                 170                 175
Thr Asn Arg Leu Gly Ser Ala Arg Ser Asp Val Leu Thr Leu Asp Val
            180                 185                 190
Leu Asp Val Val Thr Thr Asp Pro Pro Asp Val His Val Ser Arg
    195                 200                 205
Val Gly Gly Leu Glu Asp Gln Leu Ser Val Arg Trp Val Ser Pro Pro
    210                 215                 220
Ala Leu Lys Asp Phe Leu Phe Gln Ala Lys Tyr Gln Ile Arg Tyr Arg
225                 230                 235                 240
Val Glu Asp Ser Val Asp Trp Lys Val Val Asp Asp Val Ser Asn Gln
                245                 250                 255
Thr Ser Cys Arg Leu Ala Gly Leu Lys Pro Gly Thr Val Tyr Phe Val
            260                 265                 270
Gln Val Arg Cys Asn Pro Phe Gly Ile Tyr Gly Ser Lys Lys Ala Gly
    275                 280                 285
Ile Trp Ser Glu Trp Ser His Pro Thr Ala Ala Ser Thr Pro Arg Ser
    290                 295                 300
Glu Arg Pro Gly Pro Gly Gly Val Cys Glu Pro Arg Gly Gly Glu
305                 310                 315                 320
Pro Ser Ser Gly Pro Val Arg Arg Glu Leu Lys Gln Phe Leu Gly Trp
```

-continued

```
                     325                 330                 335
Leu Lys Lys His Ala Tyr Cys Ser Asn Leu Ser Phe Arg Leu Tyr Asp
            340                 345                 350
Gln Trp Arg Ala Trp Met Gln Lys Ser His Lys Thr Arg Asn Gln Asp
            355                 360                 365
Glu Gly Ile Leu Pro Ser Gly Arg Arg Gly Ala Ala Arg Gly Pro Ala
    370                 375                 380
Gly
385

(2) INFORMATION FOR SEQ ID NO:20:

(i) SEQUENCE CHARACTERISTICS:
        (A) LENGTH: 385 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:20:

Ala His Thr Ala Val Ile Ser Pro Gln Asp Pro Thr Leu Leu Ile Gly
 1               5                  10                  15
Ser Ser Leu Leu Ala Thr Cys Ser Val His Gly Asp Pro Pro Gly Ala
            20                  25                  30
Thr Ala Glu Gly Leu Tyr Trp Thr Leu Xaa Gly Arg Arg Leu Pro Pro
        35                  40                  45
Glu Leu Ser Arg Val Leu Asn Ala Ser Thr Leu Ala Leu Ala Leu Ala
    50                  55                  60
Asn Leu Asn Gly Ser Arg Gln Arg Ser Gly Asp Asn Leu Val Cys His
65                  70                  75                  80
Ala Arg Asp Gly Ser Ile Leu Ala Gly Ser Cys Leu Tyr Val Gly Leu
                85                  90                  95
Pro Pro Glu Lys Pro Val Asn Ile Ser Cys Trp Ser Lys Asn Met Lys
            100                 105                 110
Asp Leu Thr Cys Arg Trp Thr Pro Gly Ala His Gly Glu Thr Phe Leu
        115                 120                 125
His Thr Asn Tyr Ser Leu Lys Tyr Lys Leu Arg Trp Tyr Gly Gln Asp
    130                 135                 140
Asn Thr Cys Glu Glu Tyr His Thr Val Gly Pro His Ser Cys His Ile
145                 150                 155                 160
Pro Lys Asp Leu Ala Leu Phe Thr Pro Tyr Glu Ile Trp Val Glu Ala
                165                 170                 175
Thr Asn Arg Leu Gly Ser Ala Arg Ser Asp Val Leu Thr Leu Asp Ile
            180                 185                 190
Leu Asp Val Val Thr Thr Asp Pro Pro Glu Val His Val Ser Arg
        195                 200                 205
Val Gly Gly Leu Glu Asp Gln Leu Ser Val Arg Trp Val Ser Pro Pro
    210                 215                 220
Ala Leu Lys Asp Phe Leu Phe Gln Ala Lys Tyr Gln Ile Arg Tyr Arg
225                 230                 235                 240
Val Glu Asp Ser Val Asp Trp Lys Val Val Asp Val Ser Asn Gln
                245                 250                 255
Thr Ser Cys Arg Leu Ala Gly Leu Lys Pro Gly Thr Val Tyr Phe Val
            260                 265                 270
Gln Val Arg Cys Asn Pro Phe Gly Ile Tyr Gly Ser Lys Lys Ala Gly
```

-continued

```
                275                 280                 285
Ile Trp Ser Glu Trp Ser His Pro Thr Ala Ala Ser Thr Pro Arg Ser
290                 295                 300

Glu Arg Pro Gly Pro Gly Gly Gly Ala Cys Glu Pro Arg Gly Gly Glu
305                 310                 315                 320

Pro Ser Ser Gly Pro Val Arg Arg Glu Leu Lys Gln Phe Leu Gly Trp
                325                 330                 335

Leu Lys Lys His Ala Tyr Cys Ser Asn Leu Ser Phe Arg Leu Tyr Asp
                340                 345                 350

Gln Trp Arg Ala Trp Met Gln Lys Ser His Lys Thr Arg Asn Gln Asp
                355                 360                 365

Glu Gly Ile Leu Pro Ser Gly Arg Arg Gly Thr Ala Arg Gly Pro Ala
370                 375                 380

Arg
385
```

(2) INFORMATION FOR SEQ ID NO:21:

(i) SEQUENCE CHARACTERISTICS:
        (A) LENGTH: 303 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:21:

```
Ala His Thr Ala Val Ile Ser Pro Gln Asp Pro Thr Leu Leu Ile Gly
1                   5                   10                  15

Ser Ser Leu Leu Ala Thr Cys Ser Val His Gly Asp Pro Pro Gly Ala
                20                  25                  30

Thr Ala Glu Gly Leu Tyr Trp Thr Leu Asn Gly Arg Arg Leu Pro Pro
                35                  40                  45

Glu Leu Ser Arg Val Leu Asn Ala Ser Thr Leu Ala Leu Ala Leu Ala
                50                  55                  60

Asn Leu Asn Gly Ser Arg Gln Arg Ser Gly Asp Asn Leu Val Cys His
65                  70                  75                  80

Ala Arg Asp Gly Ser Ile Leu Ala Gly Ser Cys Leu Tyr Val Gly Leu
                85                  90                  95

Pro Pro Glu Lys Pro Val Asn Ile Ser Cys Trp Ser Lys Asn Met Lys
                100                 105                 110

Asp Leu Thr Cys Arg Trp Thr Pro Gly Ala His Gly Glu Thr Phe Leu
                115                 120                 125

His Thr Asn Tyr Ser Leu Lys Tyr Lys Leu Arg Trp Tyr Gly Gln Asp
                130                 135                 140

Asn Thr Cys Glu Glu Tyr His Thr Val Gly Pro His Ser Cys His Ile
145                 150                 155                 160

Pro Lys Asp Leu Ala Leu Phe Thr Pro Tyr Glu Ile Trp Val Glu Ala
                165                 170                 175

Thr Asn Arg Leu Gly Ser Ala Arg Ser Asp Val Leu Thr Leu Asp Ile
                180                 185                 190

Leu Asp Val Val Thr Thr Asp Pro Pro Glu Val His Val Ser Arg
                195                 200                 205

Val Gly Gly Leu Glu Asp Gln Leu Ser Val Arg Trp Val Ser Pro Pro
                210                 215                 220

Ala Leu Lys Asp Phe Leu Phe Gln Ala Lys Tyr Gln Ile Arg Tyr Arg
```

-continued

```
                225                 230                 235                 240
Val Glu Asp Ser Val Asp Trp Lys Val Val Asp Val Ser Asn Gln
                245                 250                 255

Thr Ser Cys Arg Leu Ala Gly Leu Lys Pro Gly Thr Val Tyr Phe Val
                260                 265                 270

Gln Val Arg Cys Asn Pro Phe Gly Ile Tyr Gly Ser Lys Lys Ala Gly
                275                 280                 285

Ile Trp Ser Glu Trp Ser His Pro Thr Ala Ala Ser Thr Pro Arg
                290                 295                 300
```

(2) INFORMATION FOR SEQ ID NO:22:

(i) SEQUENCE CHARACTERISTICS:
        (A) LENGTH: 389 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:22:

```
Ala His Thr Ala Val Ile Ser Pro Gln Asp Pro Thr Leu Leu Ile Gly
1                   5                  10                  15

Ser Ser Leu Leu Ala Thr Cys Ser Val His Gly Asp Pro Pro Gly Ala
                20                  25                  30

Thr Ala Glu Gly Leu Tyr Trp Thr Leu Asn Gly Arg Arg Leu Pro Pro
                35                  40                  45

Glu Leu Ser Arg Val Leu Asn Ala Ser Thr Leu Ala Leu Ala Leu Ala
                50                  55                  60

Asn Leu Asn Gly Ser Arg Gln Arg Ser Gly Asp Asn Leu Val Cys His
65                  70                  75                  80

Ala Arg Asp Gly Ser Ile Leu Ala Gly Ser Cys Leu Tyr Val Gly Leu
                85                  90                  95

Pro Pro Glu Lys Pro Val Asn Ile Ser Cys Trp Ser Lys Asn Met Lys
                100                 105                 110

Asp Leu Thr Cys Arg Trp Thr Pro Gly Ala His Gly Glu Thr Phe Leu
                115                 120                 125

His Thr Asn Tyr Ser Leu Lys Tyr Lys Leu Arg Trp Tyr Gly Gln Asp
                130                 135                 140

Asn Thr Cys Glu Glu Tyr His Thr Val Gly Pro His Ser Cys His Ile
145                 150                 155                 160

Pro Lys Asp Leu Ala Leu Phe Thr Pro Tyr Glu Ile Trp Val Glu Ala
                165                 170                 175

Thr Asn Arg Leu Gly Ser Ala Arg Ser Asp Val Leu Thr Leu Asp Ile
                180                 185                 190

Leu Asp Val Val Thr Thr Asp Pro Pro Asp Val His Val Ser Arg
                195                 200                 205

Val Gly Gly Leu Glu Asp Gln Leu Ser Val Arg Trp Val Ser Pro Pro
                210                 215                 220

Ala Leu Lys Asp Phe Leu Phe Gln Ala Lys Tyr Gln Ile Arg Tyr Arg
225                 230                 235                 240

Val Glu Asp Ser Val Asp Trp Lys Val Val Asp Val Ser Asn Gln
                245                 250                 255

Thr Ser Cys Arg Leu Ala Gly Leu Lys Pro Gly Thr Val Tyr Phe Val
                260                 265                 270

Gln Val Arg Cys Asn Pro Phe Gly Ile Tyr Gly Ser Lys Lys Ala Gly
```

```
            275                 280                 285
Ile Trp Ser Glu Trp Ser His Pro Thr Ala Ala Ser Thr Pro Arg Ser
    290                 295                 300

Glu Arg Pro Gly Pro Gly Gly Ala Cys Glu Pro Arg Gly Gly Glu
305                 310                 315                 320

Pro Ser Ser Gly Pro Val Arg Arg Glu Leu Lys Gln Phe Leu Gly Trp
                325                 330                 335

Leu Lys Lys His Ala Tyr Cys Ser Asn Leu Ser Phe Arg Leu Tyr Asp
                340                 345                 350

Gln Trp Arg Ala Trp Met Gln Lys Ser His Lys Thr Arg Asn Gln His
                355                 360                 365

Arg Thr Arg Gly Ser Cys Pro Arg Ala Asp Gly Ala Arg Arg Glu Val
370                 375                 380

Leu Pro Asp Lys Leu
385

(2) INFORMATION FOR SEQ ID NO:23:

(i) SEQUENCE CHARACTERISTICS:
        (A) LENGTH: 303 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:23:

Ala His Thr Ala Val Ile Ser Pro Gln Asp Pro Thr Leu Leu Ile Gly
1               5                   10                  15

Ser Ser Leu Leu Ala Thr Cys Ser Val His Gly Asp Pro Pro Gly Ala
                20                  25                  30

Thr Ala Glu Gly Leu Tyr Trp Thr Leu Asn Gly Arg Arg Leu Pro Pro
                35                  40                  45

Glu Leu Ser Arg Val Leu Asn Ala Ser Thr Leu Ala Leu Ala Leu Ala
    50                  55                  60

Asn Leu Asn Gly Ser Arg Gln Arg Ser Gly Asp Asn Leu Val Cys His
65                  70                  75                  80

Ala Arg Asp Gly Ser Ile Leu Ala Gly Ser Cys Leu Tyr Val Gly Leu
                85                  90                  95

Pro Pro Glu Lys Pro Val Asn Ile Ser Cys Trp Ser Lys Asn Met Lys
                100                 105                 110

Asp Leu Thr Cys Arg Trp Thr Pro Gly Ala His Gly Glu Thr Phe Leu
                115                 120                 125

His Thr Asn Tyr Ser Leu Lys Tyr Lys Leu Arg Trp Tyr Gly Gln Asp
                130                 135                 140

Asn Thr Cys Glu Glu Tyr His Thr Val Gly Pro His Ser Cys His Ile
145                 150                 155                 160

Pro Lys Asp Leu Ala Leu Phe Thr Pro Tyr Glu Ile Trp Val Glu Ala
                165                 170                 175

Thr Asn Arg Leu Gly Ser Ala Arg Ser Asp Val Leu Thr Leu Asp Ile
                180                 185                 190

Leu Asp Val Val Thr Thr Asp Pro Pro Asp Val His Val Ser Arg
                195                 200                 205

Val Gly Gly Leu Glu Asp Gln Leu Ser Val Arg Trp Val Ser Pro Pro
                210                 215                 220

Ala Leu Lys Asp Phe Leu Phe Gln Ala Lys Tyr Gln Ile Arg Tyr Arg
```

```
225                 230                 235                 240
Val Glu Asp Ser Val Asp Trp Lys Val Val Asp Val Ser Asn Gln
                245                 250                 255

Thr Ser Cys Arg Leu Ala Gly Leu Lys Pro Gly Thr Val Tyr Phe Val
            260                 265                 270

Gln Val Arg Cys Asn Pro Phe Gly Ile Tyr Gly Ser Lys Lys Ala Gly
            275                 280                 285

Ile Trp Ser Glu Trp Ser His Pro Thr Ala Ala Ser Thr Pro Arg
            290                 295                 300
```

(2) INFORMATION FOR SEQ ID NO:24:

(i) SEQUENCE CHARACTERISTICS:
        (A) LENGTH: 389 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:24:

```
Ala His Thr Ala Val Ile Ser Pro Gln Asp Pro Thr Leu Leu Ile Gly
1               5                   10                  15

Ser Ser Leu Leu Ala Thr Cys Ser Val His Gly Asp Pro Pro Gly Ala
            20                  25                  30

Thr Ala Glu Gly Leu Tyr Trp Thr Leu Asn Gly Arg Arg Leu Pro Pro
            35                  40                  45

Glu Leu Ser Arg Val Leu Asn Ala Ser Thr Leu Ala Leu Ala Leu Ala
50                  55                  60

Asn Leu Asn Gly Ser Arg Gln Arg Ser Gly Asp Asn Leu Val Cys His
65                  70                  75                  80

Ala Arg Asp Gly Ser Ile Leu Ala Gly Ser Cys Leu Tyr Val Gly Leu
                85                  90                  95

Pro Pro Glu Lys Pro Val Asn Ile Ser Cys Trp Ser Lys Asn Met Lys
            100                 105                 110

Asp Leu Thr Cys Arg Trp Thr Pro Gly Ser His Gly Glu Thr Phe Leu
            115                 120                 125

His Thr Asn Tyr Ser Leu Lys Tyr Lys Leu Arg Trp Tyr Gly Gln Asp
            130                 135                 140

Asn Thr Cys Glu Glu Tyr His Thr Val Gly Pro His Ser Cys His Ile
145                 150                 155                 160

Pro Lys Asp Leu Ala Leu Phe Thr Pro Tyr Glu Ile Trp Val Glu Ala
                165                 170                 175

Thr Asn Arg Leu Gly Ser Ala Arg Ser Asp Val Leu Thr Leu Asp Ile
            180                 185                 190

Leu Asp Val Val Thr Thr Asp Pro Pro Asp Val His Val Ser Arg
            195                 200                 205

Val Gly Gly Leu Glu Asp Gln Leu Ser Val Arg Trp Val Ser Pro Pro
            210                 215                 220

Ala Leu Lys Asp Phe Leu Phe Gln Ala Lys Tyr Gln Ile Arg Tyr Arg
225                 230                 235                 240

Val Glu Asp Ser Val Asp Trp Lys Val Val Asp Val Ser Asn Gln
                245                 250                 255

Thr Ser Cys Arg Leu Ala Gly Leu Lys Pro Gly Thr Val Tyr Phe Val
            260                 265                 270

Gln Val Arg Cys Asn Pro Phe Gly Ile Tyr Gly Ser Lys Lys Ala Gly
```

```
                275                 280                 285
Ile Trp Ser Glu Trp Ser His Pro Thr Ala Ala Ser Thr Pro Arg Ser
290                 295                 300

Glu Arg Pro Gly Pro Gly Gly Ala Cys Glu Pro Arg Gly Gly Glu
305                 310                 315                 320

Pro Ser Ser Gly Pro Val Arg Arg Glu Leu Lys Gln Phe Leu Gly Trp
                325                 330                 335

Leu Lys Lys His Ala Tyr Cys Ser Asn Leu Ser Phe Arg Leu Tyr Asp
                340                 345                 350

Gln Trp Arg Ala Trp Met Gln Lys Ser His Lys Thr Arg Asn Gln His
                355                 360                 365

Arg Thr Arg Gly Ser Cys Pro Arg Ala Asp Gly Ala Arg Arg Glu Val
370                 375                 380

Leu Pro Asp Lys Leu
385

(2) INFORMATION FOR SEQ ID NO:25:

(i) SEQUENCE CHARACTERISTICS:
        (A) LENGTH: 389 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:25:

Ala His Thr Ala Val Ile Ser Pro Gln Asp Pro Thr Leu Leu Ile Gly
1               5                   10                  15

Ser Ser Leu Leu Ala Thr Cys Ser Val His Gly Asp Pro Pro Gly Ala
                20                  25                  30

Thr Ala Glu Gly Leu Tyr Trp Thr Leu Asn Gly Arg Arg Leu Pro Pro
            35                  40                  45

Glu Leu Ser Arg Val Leu Asn Ala Ser Thr Leu Ala Leu Ala Leu Ala
        50                  55                  60

Asn Leu Asn Gly Ser Arg Gln Arg Ser Gly Asp Asn Leu Val Cys His
65                  70                  75                  80

Ala Arg Asp Gly Ser Ile Leu Ala Gly Ser Cys Leu Tyr Val Gly Leu
                85                  90                  95

Pro Pro Glu Lys Pro Val Asn Ile Ser Cys Trp Ser Lys Asn Met Lys
                100                 105                 110

Asp Leu Thr Cys Arg Trp Thr Pro Gly Ala His Gly Glu Thr Phe Leu
            115                 120                 125

His Thr Asn Tyr Ser Leu Lys Tyr Lys Leu Arg Trp Tyr Gly Gln Asp
        130                 135                 140

Asn Thr Cys Glu Asp Tyr His Thr Val Gly Pro His Ser Cys His Ile
145                 150                 155                 160

Pro Lys Asp Leu Ala Leu Phe Thr Pro Tyr Glu Ile Trp Val Glu Ala
                165                 170                 175

Thr Asn Arg Leu Gly Ser Ala Arg Ser Asp Val Leu Thr Leu Asp Ile
            180                 185                 190

Leu Asp Val Val Thr Thr Asp Pro Pro Asp Val His Val Ser Arg
        195                 200                 205

Val Gly Gly Leu Glu Asp Gln Leu Ser Val Arg Trp Val Ser Pro Pro
    210                 215                 220

Ala Leu Lys Asp Phe Leu Phe Gln Ala Lys Tyr Gln Ile Arg Tyr Arg
```

```
                    225                 230                 235                 240
        Val Glu Asp Ser Val Asp Trp Lys Val Val Asp Asp Val Ser Asn Gln
                        245                 250                 255
        Thr Ser Cys Arg Leu Ala Gly Leu Lys Pro Gly Thr Val Tyr Phe Val
                        260                 265                 270
        Gln Val Arg Cys Asn Pro Phe Gly Ile Tyr Gly Ser Lys Lys Ala Gly
                        275                 280                 285
        Ile Trp Ser Glu Trp Ser His Pro Thr Ala Ala Ser Thr Pro Arg Ser
                        290                 295                 300
        Glu Arg Pro Gly Pro Gly Gly Ala Cys Glu Pro Arg Gly Gly Glu
        305                 310                 315                 320
        Pro Ser Ser Gly Pro Val Arg Arg Glu Leu Lys Gln Phe Leu Gly Trp
                        325                 330                 335
        Leu Lys Lys His Ala Tyr Cys Ser Asn Leu Ser Phe Arg Leu Tyr Asp
                        340                 345                 350
        Gln Trp Arg Ala Trp Met Gln Lys Ser His Lys Thr Arg Asn Gln His
                        355                 360                 365
        Arg Thr Arg Gly Ser Cys Pro Arg Ala Asp Gly Ala Arg Arg Glu Val
                        370                 375                 380
        Leu Pro Asp Lys Leu
        385

(2) INFORMATION FOR SEQ ID NO:26:

(i) SEQUENCE CHARACTERISTICS:
            (A) LENGTH: 389 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:26:

Ala His Thr Ala Val Ile Ser Pro Gln Asp Pro Thr Leu Leu Ile Gly
        1               5                   10                  15

Ser Ser Leu Leu Ala Thr Cys Ser Val His Gly Asp Pro Pro Gly Ala
                        20                  25                  30

Thr Ala Glu Gly Leu Tyr Trp Thr Leu Asn Gly Arg Arg Leu Pro Pro
                        35                  40                  45

Glu Leu Ser Arg Val Leu Asn Ala Ser Thr Leu Ala Leu Ala Leu Ala
        50                  55                  60

Asn Leu Asn Gly Ser Arg Gln Arg Ser Gly Asp Asn Leu Val Cys His
        65                  70                  75                  80

Ala Arg Asp Gly Ser Ile Leu Ala Gly Ser Cys Leu Tyr Val Gly Leu
                        85                  90                  95

Pro Pro Glu Lys Pro Val Asn Ile Ser Cys Trp Ser Lys Asn Met Lys
                        100                 105                 110

Asp Leu Thr Cys Arg Trp Thr Pro Gly Ala His Gly Glu Thr Phe Leu
                        115                 120                 125

His Thr Asn Tyr Ser Leu Lys Tyr Lys Leu Arg Trp Tyr Gly Gln Asp
                        130                 135                 140

Asn Thr Cys Glu Glu Tyr His Thr Val Gly Pro His Ser Cys His Ile
        145                 150                 155                 160

Pro Lys Asp Leu Thr Leu Phe Thr Pro Tyr Glu Ile Trp Val Glu Ala
                        165                 170                 175

Thr Asn Arg Leu Gly Ser Ala Arg Ser Asp Val Leu Thr Leu Asp Ile
```

-continued

```
                180                 185                 190
Leu Asp Val Val Thr Asp Pro Pro Asp Val His Val Ser Arg
            195                 200                 205
Val Gly Gly Leu Glu Asp Gln Leu Ser Val Arg Trp Val Ser Pro Pro
210                 215                 220
Ala Leu Lys Asp Phe Leu Phe Gln Ala Lys Tyr Gln Ile Arg Tyr Arg
225                 230                 235                 240
Val Glu Asp Ser Val Asp Trp Lys Val Val Asp Val Ser Asn Gln
            245                 250                 255
Thr Ser Cys Arg Leu Ala Gly Leu Lys Pro Gly Thr Val Tyr Phe Val
            260                 265                 270
Gln Val Arg Cys Asn Pro Phe Gly Ile Tyr Gly Ser Lys Lys Ala Gly
            275                 280                 285
Ile Trp Ser Glu Trp Ser His Pro Thr Ala Ala Ser Thr Pro Arg Ser
290                 295                 300
Glu Arg Pro Gly Pro Gly Gly Ala Cys Glu Pro Arg Gly Gly Glu
305                 310                 315                 320
Pro Ser Ser Gly Pro Val Arg Arg Glu Leu Lys Gln Phe Leu Gly Trp
            325                 330                 335
Leu Lys Lys His Ala Tyr Cys Ser Asn Leu Ser Phe Arg Leu Tyr Asp
            340                 345                 350
Gln Trp Arg Ala Trp Met Gln Lys Ser His Lys Thr Arg Asn Gln His
            355                 360                 365
Arg Thr Arg Gly Ser Cys Pro Arg Ala Asp Gly Ala Arg Arg Glu Val
            370                 375                 380
Leu Pro Asp Lys Leu
385
```

(2) INFORMATION FOR SEQ ID NO:27:

(i) SEQUENCE CHARACTERISTICS:
        (A) LENGTH: 389 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:27:

```
Ala His Thr Ala Val Ile Ser Pro Gln Asp Pro Thr Leu Leu Ile Gly
1               5                   10                  15
Ser Ser Leu Leu Ala Thr Cys Ser Val His Gly Asp Pro Pro Gly Ala
            20                  25                  30
Thr Ala Glu Gly Leu Tyr Trp Thr Leu Asn Gly Arg Arg Leu Pro Pro
            35                  40                  45
Glu Leu Ser Arg Val Leu Asn Ala Ser Thr Leu Ala Leu Ala Leu Ala
50                  55                  60
Asn Leu Asn Gly Ser Arg Gln Arg Ser Gly Asp Asn Leu Val Cys His
65                  70                  75                  80
Ala Arg Asp Gly Ser Ile Leu Ala Gly Ser Cys Leu Tyr Val Gly Leu
            85                  90                  95
Pro Pro Glu Lys Pro Val Asn Ile Ser Cys Trp Ser Lys Asn Met Lys
            100                 105                 110
Asp Leu Thr Cys Arg Trp Thr Pro Gly Ala His Gly Glu Thr Phe Leu
            115                 120                 125
His Thr Asn Tyr Ser Leu Lys Tyr Lys Leu Arg Trp Tyr Gly Gln Asp
```

```
                130              135              140
Asn Thr Cys Glu Glu Tyr His Thr Val Gly Pro His Ser Cys His Ile
145                 150                 155                 160

Pro Lys Asp Leu Ala Leu Phe Thr Pro Tyr Glu Ile Trp Val Glu Ala
                165                 170                 175

Thr Asn Arg Leu Gly Ser Ser Arg Ser Asp Val Leu Thr Leu Asp Ile
                180                 185                 190

Leu Asp Val Val Thr Thr Asp Pro Pro Pro Asp Val His Val Ser Arg
                195                 200                 205

Val Gly Gly Leu Glu Asp Gln Leu Ser Val Arg Trp Val Ser Pro Pro
                210                 215                 220

Ala Leu Lys Asp Phe Leu Phe Gln Ala Lys Tyr Gln Ile Arg Tyr Arg
225                 230                 235                 240

Val Glu Asp Ser Val Asp Trp Lys Val Asp Asp Val Ser Asn Gln
                245                 250                 255

Thr Ser Cys Arg Leu Ala Gly Leu Lys Pro Gly Thr Val Tyr Phe Val
                260                 265                 270

Gln Val Arg Cys Asn Pro Phe Gly Ile Tyr Gly Ser Lys Lys Ala Gly
                275                 280                 285

Ile Trp Ser Glu Trp Ser His Pro Thr Ala Ala Ser Thr Pro Arg Ser
290                 295                 300

Glu Arg Pro Gly Pro Gly Gly Ala Cys Glu Pro Arg Gly Gly Glu
305                 310                 315                 320

Pro Ser Ser Gly Pro Val Arg Arg Glu Leu Lys Gln Phe Leu Gly Trp
                325                 330                 335

Leu Lys Lys His Ala Tyr Cys Ser Asn Leu Ser Phe Arg Leu Tyr Asp
                340                 345                 350

Gln Trp Arg Ala Trp Met Gln Lys Ser His Lys Thr Arg Asn Gln His
                355                 360                 365

Arg Thr Arg Gly Ser Cys Pro Arg Ala Asp Gly Ala Arg Arg Glu Val
370                 375                 380

Leu Pro Asp Lys Leu
385

(2) INFORMATION FOR SEQ ID NO:28:

(i) SEQUENCE CHARACTERISTICS:
        (A) LENGTH: 389 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:28:

Ala His Thr Ala Val Ile Ser Pro Gln Asp Pro Thr Leu Leu Ile Gly
1               5                   10                  15

Ser Ser Leu Leu Ala Thr Cys Ser Val His Gly Asp Pro Pro Gly Ala
                20                  25                  30

Thr Ala Glu Gly Leu Tyr Trp Thr Leu Asn Gly Arg Arg Leu Pro Pro
                35                  40                  45

Glu Leu Ser Arg Val Leu Asn Ala Ser Thr Leu Ala Leu Ala Leu Ala
            50                  55                  60

Asn Leu Asn Gly Ser Arg Gln Arg Ser Gly Asp Asn Leu Val Cys His
65                  70                  75                  80

Ala Arg Asp Gly Ser Ile Leu Ala Gly Ser Cys Leu Tyr Val Gly Leu
```

-continued

```
                    85                  90                  95
Pro Pro Glu Lys Pro Val Asn Ile Ser Cys Trp Ser Lys Asn Met Lys
                100                 105                 110

Asp Leu Thr Cys Arg Trp Thr Pro Gly Ala His Gly Glu Thr Phe Leu
                115                 120                 125

His Thr Asn Tyr Ser Leu Lys Tyr Lys Leu Arg Trp Tyr Gly Gln Asp
                130                 135                 140

Asn Thr Cys Glu Glu Tyr His Thr Val Gly Pro His Ser Cys His Ile
145                 150                 155                 160

Pro Lys Asp Leu Ala Leu Phe Thr Pro Tyr Glu Ile Trp Val Glu Ala
                165                 170                 175

Thr Asn Arg Leu Gly Ser Ala Arg Ser Asp Val Leu Thr Leu Asp Val
                180                 185                 190

Leu Asp Val Val Thr Thr Asp Pro Pro Asp Val His Val Ser Arg
                195                 200                 205

Val Gly Gly Leu Glu Asp Gln Leu Ser Val Arg Trp Val Ser Pro Pro
                210                 215                 220

Ala Leu Lys Asp Phe Leu Phe Gln Ala Lys Tyr Gln Ile Arg Tyr Arg
225                 230                 235                 240

Val Glu Asp Ser Val Asp Trp Lys Val Val Asp Asp Val Ser Asn Gln
                245                 250                 255

Thr Ser Cys Arg Leu Ala Gly Leu Lys Pro Gly Thr Val Tyr Phe Val
                260                 265                 270

Gln Val Arg Cys Asn Pro Phe Gly Ile Tyr Gly Ser Lys Lys Ala Gly
                275                 280                 285

Ile Trp Ser Glu Trp Ser His Pro Thr Ala Ala Ser Thr Pro Arg Ser
                290                 295                 300

Glu Arg Pro Gly Pro Gly Gly Ala Cys Glu Pro Arg Gly Gly Glu
305                 310                 315                 320

Pro Ser Ser Gly Pro Val Arg Arg Glu Leu Lys Gln Phe Leu Gly Trp
                325                 330                 335

Leu Lys Lys His Ala Tyr Cys Ser Asn Leu Ser Phe Arg Leu Tyr Asp
                340                 345                 350

Gln Trp Arg Ala Trp Met Gln Lys Ser His Lys Thr Arg Asn Gln His
                355                 360                 365

Arg Thr Arg Gly Ser Cys Pro Arg Ala Asp Gly Ala Arg Arg Glu Val
370                 375                 380

Leu Pro Asp Lys Leu
385

(2) INFORMATION FOR SEQ ID NO:29:

(i) SEQUENCE CHARACTERISTICS:
        (A) LENGTH: 389 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:29:

Ala His Thr Ala Val Ile Ser Pro Gln Asp Pro Thr Leu Leu Ile Gly
 1                  5                  10                  15

Ser Ser Leu Leu Ala Thr Cys Ser Val His Gly Asp Pro Pro Gly Ala
                20                  25                  30

Thr Ala Glu Gly Leu Tyr Trp Thr Leu Asn Gly Arg Arg Leu Pro Pro
```

```
            35                  40                  45
Glu Leu Ser Arg Val Leu Asn Ala Ser Thr Leu Ala Leu Ala
    50                  55                  60

Asn Leu Asn Gly Ser Arg Gln Arg Ser Gly Asp Asn Leu Val Cys His
65                  70                  75                  80

Ala Arg Asp Gly Ser Ile Leu Ala Gly Ser Cys Leu Tyr Val Gly Leu
                85                  90                  95

Pro Pro Glu Lys Pro Val Asn Ile Ser Cys Trp Ser Lys Asn Met Lys
            100                 105                 110

Asp Leu Thr Cys Arg Trp Thr Pro Gly Ala His Gly Glu Thr Phe Leu
            115                 120                 125

His Thr Asn Tyr Ser Leu Lys Tyr Lys Leu Arg Trp Tyr Gly Gln Asp
    130                 135                 140

Asn Thr Cys Glu Glu Tyr His Thr Val Gly Pro His Ser Cys His Ile
145                 150                 155                 160

Pro Lys Asp Leu Ala Leu Phe Thr Pro Tyr Glu Ile Trp Val Glu Ala
                165                 170                 175

Thr Asn Arg Leu Gly Ser Ala Arg Ser Asp Val Leu Thr Leu Asp Ile
            180                 185                 190

Leu Asp Ile Val Thr Thr Asp Pro Pro Asp Val His Val Ser Arg
        195                 200                 205

Val Gly Gly Leu Glu Asp Gln Leu Ser Val Arg Trp Val Ser Pro Pro
    210                 215                 220

Ala Leu Lys Asp Phe Leu Phe Gln Ala Lys Tyr Gln Ile Arg Tyr Arg
225                 230                 235                 240

Val Glu Asp Ser Val Asp Trp Lys Val Val Asp Asp Val Ser Asn Gln
                245                 250                 255

Thr Ser Cys Arg Leu Ala Gly Leu Lys Pro Gly Thr Val Tyr Phe Val
            260                 265                 270

Gln Val Arg Cys Asn Pro Phe Gly Ile Tyr Gly Ser Lys Lys Ala Gly
            275                 280                 285

Ile Trp Ser Glu Trp Ser His Pro Thr Ala Ala Ser Thr Pro Arg Ser
    290                 295                 300

Glu Arg Pro Gly Pro Gly Gly Ala Cys Glu Pro Arg Gly Gly Glu
305                 310                 315                 320

Pro Ser Ser Gly Pro Val Arg Arg Glu Leu Lys Gln Phe Leu Gly Trp
                325                 330                 335

Leu Lys Lys His Ala Tyr Cys Ser Asn Leu Ser Phe Arg Leu Tyr Asp
            340                 345                 350

Gln Trp Arg Ala Trp Met Gln Lys Ser His Lys Thr Arg Asn Gln His
    355                 360                 365

Arg Thr Arg Gly Ser Cys Pro Arg Ala Asp Gly Ala Arg Arg Glu Val
370                 375                 380

Leu Pro Asp Lys Leu
385

(2) INFORMATION FOR SEQ ID NO:30:

(i) SEQUENCE CHARACTERISTICS:
        (A) LENGTH: 389 amino acids
        (B) TYPE: amino acid
        (C) STRANDEDNESS: single
        (D) TOPOLOGY: linear (ii) MOLECULE TYPE: protein
```

(xi) SEQUENCE DESCRIPTION: SEQ ID NO:30:

```
Ala His Thr Ala Val Ile Ser Pro Gln Asp Pro Thr Leu Leu Ile Gly
 1               5                  10                  15

Ser Ser Leu Leu Ala Thr Cys Ser Val His Gly Asp Pro Pro Gly Ala
                20                  25                  30

Thr Ala Glu Gly Leu Tyr Trp Thr Leu Asn Gly Arg Arg Leu Pro Pro
            35                  40                  45

Glu Leu Ser Arg Val Leu Asn Ala Ser Thr Leu Ala Leu Ala Leu Ala
        50                  55                  60

Asn Leu Asn Gly Ser Arg Gln Arg Ser Gly Asp Asn Leu Val Cys His
 65                  70                  75                  80

Ala Arg Asp Gly Ser Ile Leu Ala Gly Ser Cys Leu Tyr Val Gly Leu
                85                  90                  95

Pro Pro Glu Lys Pro Val Asn Ile Ser Cys Trp Ser Lys Asn Met Lys
                100                 105                 110

Asp Leu Thr Cys Arg Trp Thr Pro Gly Ala His Gly Glu Thr Phe Leu
            115                 120                 125

His Thr Asn Tyr Ser Leu Lys Tyr Lys Leu Arg Trp Tyr Gly Gln Asp
        130                 135                 140

Asn Thr Cys Glu Glu Tyr His Thr Val Gly Pro His Ser Cys His Ile
145                 150                 155                 160

Pro Lys Asp Leu Ala Leu Phe Thr Pro Tyr Glu Ile Trp Val Glu Ala
                165                 170                 175

Thr Asn Arg Leu Gly Ser Ala Arg Ser Asp Val Leu Thr Leu Asp Ile
            180                 185                 190

Leu Asp Val Val Thr Thr Asp Pro Pro Asp Val His Val Ser Arg
        195                 200                 205

Val Gly Gly Leu Glu Asp Gln Leu Ser Val Arg Trp Val Ser Pro Pro
    210                 215                 220

Ala Leu Lys Asp Phe Leu Phe Gln Ala Lys Tyr Gln Ile Arg Tyr Arg
225                 230                 235                 240

Val Glu Asp Ser Val Asp Trp Lys Val Val Asp Asp Val Ser Asn Gln
                245                 250                 255

Thr Ser Cys Arg Ile Ala Gly Leu Lys Pro Gly Thr Val Tyr Phe Val
            260                 265                 270

Gln Val Arg Cys Asn Pro Phe Gly Ile Tyr Gly Ser Lys Lys Ala Gly
        275                 280                 285

Ile Trp Ser Glu Trp Ser His Pro Thr Ala Ala Ser Thr Pro Arg Ser
290                 295                 300

Glu Arg Pro Gly Pro Gly Gly Gly Ala Cys Glu Pro Arg Gly Gly Glu
305                 310                 315                 320

Pro Ser Ser Gly Pro Val Arg Arg Glu Leu Lys Gln Phe Leu Gly Trp
                325                 330                 335

Leu Lys Lys His Ala Tyr Cys Ser Asn Leu Ser Phe Arg Leu Tyr Asp
            340                 345                 350

Gln Trp Arg Ala Trp Met Gln Lys Ser His Lys Thr Arg Asn Gln His
        355                 360                 365

Arg Thr Arg Gly Ser Cys Pro Arg Ala Asp Gly Ala Arg Arg Glu Val
370                 375                 380

Leu Pro Asp Lys Leu
385
```

(2) INFORMATION FOR SEQ ID NO:31:

(i) SEQUENCE CHARACTERISTICS:
  (A) LENGTH: 389 amino acids
  (B) TYPE: amino acid
  (C) STRANDEDNESS: single
  (D) TOPOLOGY: linear (ii) MOLECULE TYPE: protein (xi) SEQUENCE DESCRIPTION: SEQ ID NO:31:

```
Ala His Thr Ala Val Ile Ser Pro Gln Asp Pro Thr Leu Leu Ile Gly
1               5                   10                  15

Ser Ser Leu Leu Ala Thr Cys Ser Val His Gly Asp Pro Pro Gly Ala
            20                  25                  30

Thr Ala Glu Gly Leu Tyr Trp Thr Leu Asn Gly Arg Arg Leu Pro Pro
        35                  40                  45

Glu Leu Ser Arg Val Leu Asn Ala Ser Thr Leu Ala Leu Ala Leu Ala
    50                  55                  60

Asn Leu Asn Gly Ser Arg Gln Arg Ser Gly Asp Asn Leu Val Cys His
65                  70                  75                  80

Ala Arg Asp Gly Ser Ile Leu Ala Gly Ser Cys Leu Tyr Val Gly Leu
                85                  90                  95

Pro Pro Glu Lys Pro Val Asn Ile Ser Cys Trp Ser Lys Asn Met Lys
            100                 105                 110

Asp Leu Thr Cys Arg Trp Thr Pro Gly Ala His Gly Glu Thr Phe Leu
        115                 120                 125

His Thr Asn Tyr Ser Leu Lys Tyr Lys Leu Arg Trp Tyr Gly Gln Asp
    130                 135                 140

Asn Thr Cys Glu Glu Tyr His Thr Val Gly Pro His Ser Cys His Ile
145                 150                 155                 160

Pro Lys Asp Leu Ala Leu Phe Thr Pro Tyr Glu Ile Trp Val Glu Ala
                165                 170                 175

Thr Asn Arg Leu Gly Ser Ala Arg Ser Asp Val Leu Thr Leu Asp Ile
            180                 185                 190

Leu Asp Val Val Thr Thr Asp Pro Pro Asp Val His Val Ser Arg
        195                 200                 205

Val Gly Gly Leu Glu Asp Gln Leu Ser Val Arg Trp Val Ser Pro Pro
210                 215                 220

Ala Leu Lys Asp Phe Leu Phe Gln Ala Lys Tyr Gln Ile Arg Tyr Arg
225                 230                 235                 240

Val Glu Asp Ser Val Asp Trp Lys Val Val Asp Val Ser Asn Gln
                245                 250                 255

Thr Ser Cys Arg Leu Ile Gly Leu Lys Pro Gly Thr Val Tyr Phe Val
            260                 265                 270

Gln Val Arg Cys Asn Pro Phe Gly Ile Tyr Gly Ser Lys Lys Ala Gly
        275                 280                 285

Ile Trp Ser Glu Trp Ser His Pro Thr Ala Ala Ser Thr Pro Arg Ser
290                 295                 300

Glu Arg Pro Gly Pro Gly Gly Ala Cys Glu Pro Arg Gly Gly Glu
305                 310                 315                 320

Pro Ser Ser Gly Pro Val Arg Arg Glu Leu Lys Gln Phe Leu Gly Trp
                325                 330                 335

Leu Lys Lys His Ala Tyr Cys Ser Asn Leu Ser Phe Arg Leu Tyr Asp
            340                 345                 350

Gln Trp Arg Ala Trp Met Gln Lys Ser His Lys Thr Arg Asn Gln His
        355                 360                 365
```

```
Arg Thr Arg Gly Ser Cys Pro Arg Ala Asp Gly Ala Arg Arg Glu Val
    370                 375                 380

Leu Pro Asp Lys Leu
385
```

(2) INFORMATION FOR SEQ ID NO:32:

(i) SEQUENCE CHARACTERISTICS:
        (A) LENGTH: 48 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:32:

```
Asn Ser Ala Arg Gly Ala Cys Val Pro Arg Arg Ala Pro Pro Pro Pro
1               5                   10                  15

Ser Arg Ser Pro Pro Arg Ala Pro Gly Ser Ala Gly Pro Met Pro Ala
                20                  25                  30

Gly Pro Met Pro Ala Gly Arg Arg Gly Pro Ala Ala Gln Ser Ala Arg
            35                  40                  45
```

(2) INFORMATION FOR SEQ ID NO:33:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:33:

```
Asn Ser Ala Arg Gly Ala Cys Val Pro Arg Arg Ala Pro Pro Pro Pro
1               5                   10                  15

Ser Arg Ser Pro Pro Arg Ala Pro Gly Ser
                20                  25
```

(2) INFORMATION FOR SEQ ID NO:34:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:34:

```
Ala Gly Pro Met Pro Ala Gly Pro Met Pro Ala Gly Arg Arg Gly Pro
1               5                   10                  15

Ala Ala Gln Ser Ala Arg
            20
```

(2) INFORMATION FOR SEQ ID NO:35:

(i) SEQUENCE CHARACTERISTICS:
        (A) LENGTH: 32 amino acids
        (B) TYPE: amino acid
        (C) STRANDEDNESS: single
        (D) TOPOLOGY: linear (xi) SEQUENCE DESCRIPTION: SEQ ID NO:35:

```
Ser Pro Pro Ala Leu Lys Asp Phe Leu Phe Gln Ala Lys Tyr Gln Ile
```

```
                1               5                  10                 15
            Arg Tyr Arg Val Glu Asp Ser Val Asp Trp Lys Val Val Asp Asp Val
                            20                  25                  30
```

(2) INFORMATION FOR SEQ ID NO:36:

(i) SEQUENCE CHARACTERISTICS:
        (A) LENGTH: 31 amino acids
        (B) TYPE: amino acid
        (C) STRANDEDNESS: single
        (D) TOPOLOGY: linear (xi) SEQUENCE DESCRIPTION: SEQ ID NO:36:

```
Ala Ala Ser Thr Pro Arg Ser Glu Arg Pro Gly Pro Gly Gly Ala
 1               5                  10                  15

Cys Glu Pro Arg Gly Gly Glu Pro Ser Ser Gly Pro Val Arg Arg
                20                  25                  30
```

(2) INFORMATION FOR SEQ ID NO:37:

(i) SEQUENCE CHARACTERISTICS:
        (A) LENGTH: 29 amino acids
        (B) TYPE: amino acid
        (C) STRANDEDNESS: single
        (D) TOPOLOGY: linear (xi) SEQUENCE DESCRIPTION: SEQ ID NO:37:

```
Trp Met Gln Lys Ser His Lys Thr Arg Asn Gln Asp Glu Gly Ile Leu
 1               5                  10                  15

Pro Ser Gly Arg Arg Gly Thr Ala Arg Gly Pro Ala Arg
                20                  25
```